United States Patent
Han et al.

(12) 
(10) Patent No.: US 11,078,217 B2
(45) Date of Patent: Aug. 3, 2021

(54) TRIPLET-TRIPLET ANNIHILATION UPCONVERSION SYSTEM, AND COMPOSITIONS AND METHODS THEREOF FOR DRUG DELIVERY

(71) Applicant: University of Massachusetts, Boston, MA (US)

(72) Inventors: Gang Han, Shrewsbury, MA (US); Ling Huang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/641,559

(22) PCT Filed: Sep. 2, 2018

(86) PCT No.: PCT/US2018/049291
§ 371 (c)(1),
(2) Date: Feb. 24, 2020

(87) PCT Pub. No.: WO2019/050812
PCT Pub. Date: Mar. 14, 2019

(65) Prior Publication Data
US 2020/0172559 A1    Jun. 4, 2020

Related U.S. Application Data

(60) Provisional application No. 62/554,174, filed on Sep. 5, 2017.

(51) Int. Cl.
*C07F 5/02* (2006.01)
*A61K 47/54* (2017.01)
*A61K 47/69* (2017.01)
*A61K 31/196* (2006.01)
*A61K 41/00* (2020.01)
*B82Y 5/00* (2011.01)

(52) U.S. Cl.
CPC ............ *C07F 5/022* (2013.01); *A61K 31/196* (2013.01); *A61K 41/0042* (2013.01); *A61K 47/558* (2017.08); *A61K 47/6929* (2017.08); *B82Y 5/00* (2013.01)

(58) Field of Classification Search
CPC ... C07F 5/022; A61K 47/558; A61K 47/6929; A61K 31/196; A61K 41/0042; A61K 47/6923; A61K 31/00; B82Y 5/00; C09B 23/0008; C09B 23/04; C09B 23/12; C09B 57/00
See application file for complete search history.

(56) References Cited

PUBLICATIONS

Wu Organic Triplet Sensitizer JOC, p. 7056 (Year: 2011).*
Lin Mesoporous Silica JACS p. 10645 (Year: 2010).*

* cited by examiner

*Primary Examiner* — Matthew P Coughlin
*Assistant Examiner* — Thurman Wheeler
(74) *Attorney, Agent, or Firm* — Milstein Zhang & Wu LLC

(57) ABSTRACT

The invention provides a novel class of materials that possess triplet-triplet annihilation upconversion, compositions and methods of preparation and use thereof. The invention also relates to use of such materials and nanoparticles, for example, in stimulus-responsive, in situ delivery of biologically active agents.

17 Claims, 22 Drawing Sheets

TRIPLET-TRIPLET ANNIHILATION UPCONVERSION SYSTEM, AND COMPOSITIONS AND METHODS THEREOF FOR DRUG DELIVERY

PRIORITY CLAIMS AND RELATED APPLICATIONS

This application is the U.S. national phase of and claims priority to PCT/US18/49291, filed Sep. 2, 2018, which claims the benefit of priority from U.S. Provisional Application Ser. No. 62/554,174, filed on Sep. 5, 2017, the entire content of each of which is incorporated herein by reference.

TECHNICAL FIELDS OF THE INVENTION

The invention generally relates to nano-materials and compositions. More particularly, the invention relates to a novel class of materials characterized by triplet-triplet annihilation upconversion, compositions and methods of preparation and use thereof. The invention also relates to use of such materials and nanoparticles for stimulus-responsive, in situ delivery of biologically active agents.

BACKGROUND OF THE INVENTION

Recently, stimulus-responsive prodrug release and delivery systems have attracted growing interest in the fields of chemistry and biology. Studies have shown improved therapeutic efficacy from drug release in malignant sites with minimal off-targeting side effects. (Brieke, et al. 2012 *Angew. Chem. Int. Ed.* 51, 8446-8476; Bort, et al. 2013 *Angew. Chem. Int. Ed.* 52, 4526-4537; Fan, et al. 2012 *Angew. Chem. Int. Ed.* 51, 8806-8810.) Compared to other drug release strategies, light-induced prodrug activation is unique, with noninvasive operations and high spatiotemporal controllability. (Croissant, et al. 2013 *Angew. Chem. Int. Ed.* 52, 13813-13817; Fenno, et al. 2011 *Annu. Rev. Neurosci.* 34, 389-412; Huebsch, et al. 2014 *Proc. Natl. Acad. Sci. USA*. 111, 9762-9767.)

In light-induced prodrug activation, drug molecules are typically modified and protected with light sensitive chromophores, such as coumarin, 2-nitrobenzyl and 7-nitroindoline. However, these chromophores typically require short wavelength, e.g., deep blue light (435 nm) or phototoxic ultraviolet (UV) light (365 nm), as the excitation light sources, which unfortunately suffer from rather poor tissue penetration depth in in vivo applications. (Chen et al. 2012 *ACS Nano.* 6, 8280-8287; Wu et al. 2015 *Bioconjugate. Chem.* 26, 166-175; Yang, et al. 2015 *Chem. Soc. Rev.* 44, 1416-1448; Zheng, et al. 2015 *Chem. Soc. Rev.* 44, 1379-1415.)

To address such shortcomings, long wavelength light has recently been utilized in the therapeutic window (600-900 nm) due to its minimal absorption by tissue and deep tissue penetration. (Goswami, et al. 2015 *J. Am. Chem. Soc.* 137, 3783-3786; Jana, et al. 2014 *ACS Nano.* 8, 5939-5952; Klan, et al. 2013 *Chem. Rev.*, 113, 119-191; Pellois et al. 2005 *Angew. Chem. Int. Ed.* 44, 5713-5717; Trenor, et al. 2004 *Chem. Rev.* 104, 3059-3077.) For example, lanthanide ion-doped inorganic upconversion nanoparticles (UCNPs) have the ability to convert tissue penetrable long wavelength light into high-energy short wavelength photons in order to trigger small molecule drug release. (Yang, et al. 2015 *Chem. Soc. Rev.* 44, 1416-1448; Goswami, et al. 2015 *J. Am. Chem. Soc.* 137, 3783-3786.)

Challenges remain, however, in regard to inorganic UCNPs. For instance, due to the intrinsic low absorption and emission cross-sections of the contained lanthanide ions, such UCNPs have low quantum yields that typically require high power density laser excitation. In addition, the long-term in vivo toxicity and systematic clearance of inorganic lanthanide ions inside UCNPs are unknown. (Zheng, et al. *Chem. Soc. Rev.* 2015, 44, 1379-1415; Gnach, et al. *Chem. Soc. Rev.* 2015, 44, 1561-1584; Sun, et al. *Chem. Soc. Rev.* 2015, 44, 1509-1525.)

Thus, there is an ongoing need for novel materials and improved upconversion that are suitable for stimulus-responsive, in situ delivery of biologically active agents thereof.

SUMMARY OF THE INVENTION

The invention provides a novel class of materials that possess triplet-triplet annihilation upconversion, and compositions and methods of preparation thereof. The invention additionally provides method for using such materials and nanoparticles thereof for stimulus-responsive, in situ delivery of biologically active agents for a wide range of clinical applications.

A key aspect of the present invention is the unconventional strategy to expand anti-Stokes shift from the red region or far-red region to the deep-blue region in a metal-free, triplet-triplet annihilation upconversion (TTA-UC) strategy.

Another key aspect of the invention is the in vivo photo-triggered release of a therapeutic agent, e.g., an anticancer prodrug, upon delivery to a target disease site.

The TTA system disclosed herein exhibits robust brightness and, to our knowledge, the longest anti-Stokes shift of any reported TTA system. Also disclosed herein are TTA core-shell-structured prodrug delivery capsules that can operate with low-power-density red or far-red light-emitting diode (LED) light.

For example, capsules are disclosed that contain mesoporous silica nanoparticles preloaded with TTA molecules as the core and amphiphilic polymers encapsulating anticancer prodrug molecules as the shell. When stimulated by red or far-red light, the intense TTA upconversion blue emission in the system activates the anticancer prodrug molecules and shows effective tumor growth inhibition in vivo.

As promising alternatives to inorganic UC systems, the disclosed invention paves the way for the utilization of organic TTA upconversion in photocontrollable in vivo drug release and other biophotonic applications.

In one aspect, the invention generally relates to an upconversion composition, comprising an organic triplet photosensitizer molecule and an organic emitter molecule, wherein the composition is characterized by an upconversion upon excitation in the red region of about 500 nm to about 600 nm or far red region of about 600 nm to about 700 nm with an emission in the deep blue region of about 410 nm to about 550 nm, wherein each of the triplet photosensitizer and emitter molecules comprises no metallic elements.

In another aspect, the invention generally relates to a compound having the structural formula (I):

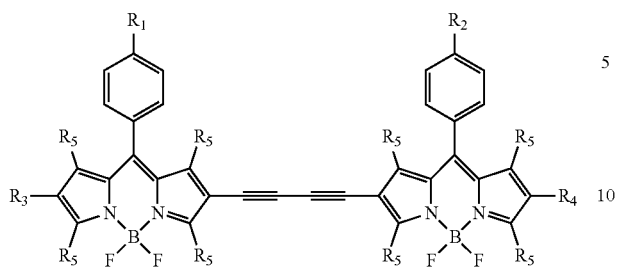

wherein each of $R_1$ and $R_2$ is independently selected from the group consisting of: H, bromo, iodio, alkynyl, alkyl, alkenyl, azide, PEG, amino, carboxyl acid and hydroxyl;

$R_3$ is selected from the group consisting of: bromo and iodio;

$R_4$ is an arylethynyl group; and each $R_5$ is independently selected from the group consisting of: H and alkyl.

In yet another aspect, the invention generally relates to a biocompatible nanoparticle delivery system. The system includes: a triplet photosensitizer molecule and an emitter molecule, wherein each of the triplet photosensitizer and emitter molecules is an organic molecule and comprises no metallic elements; the triplet photosensitizer is excited by a light in the red region of about 500 nm to about 600 nm or far red region of about 600 nm to about 700 nm causing an emission by the emitter molecule in the deep-blue region of about 410 nm to about 550 nm; and a photolabile molecule comprising a biologically active agent, wherein the biologically active agent is releasable upon absorption of the emission by the emitter molecule.

In yet another aspect, the invention generally relates to a pharmaceutical composition comprising a compound or a nanoparticle delivery system disclosed herein.

In yet another aspect, the invention generally relates to a method for delivery of a bioactive agent to a target site. The method includes: administering to a subject in need thereof a biocompatible nanoparticle comprising: a triplet photosensitizer molecule and an emitter molecule, wherein each of the triplet photosensitizer and emitter molecules is an organic molecule and comprises no metallic elements; the triplet photosensitizer is excited by a light in the red region of about 500 nm to about 600 nm or far red region of about 600 nm to about 700 nm causing an emission by the emitter molecule in the deep blue region of about 410 nm to about 550 nm; and a photolabile molecule comprising a biologically active agent, wherein the biologically active agent is releasable upon absorption of the emission by the emitter molecule, and irradiating the target site with a light beam in the red region of about 500 nm to about 600 nm or far red region of about 600 nm to about 700 nm, thereby causing the release of the biologically active agent at the target site.

In yet another aspect, the invention generally relates to a method for treating tumor or cancer. The method includes: administering to a subject in need thereof an effective amount of a biocompatible nanoparticle comprising: a triplet photosensitizer molecule and an emitter molecule, wherein each of the triplet photosensitizer and emitter molecules is an organic molecule and comprises no metallic elements; the triplet photosensitizer is excited by a light in the red region of about 500 nm to about 600 nm or far red region of about 600 nm to about 700 nm causing an emission by the emitter molecule in the deep blue region of about 410 nm to about 500 nm; and a photolabile molecule comprising an antitumor or anticancer agent, wherein the antitumor or anticancer is releasable upon absorption of the emission by the emitter molecule, and irradiating the target site with a light beam in the red region of about 500 nm to about 600 nm or far red region of about 600 nm to about 700 nm, thereby causing the release of the antitumor or anticancer agent at the target site.

DETAILED DESCRIPTION OF THE INVENTION

Figure 1:
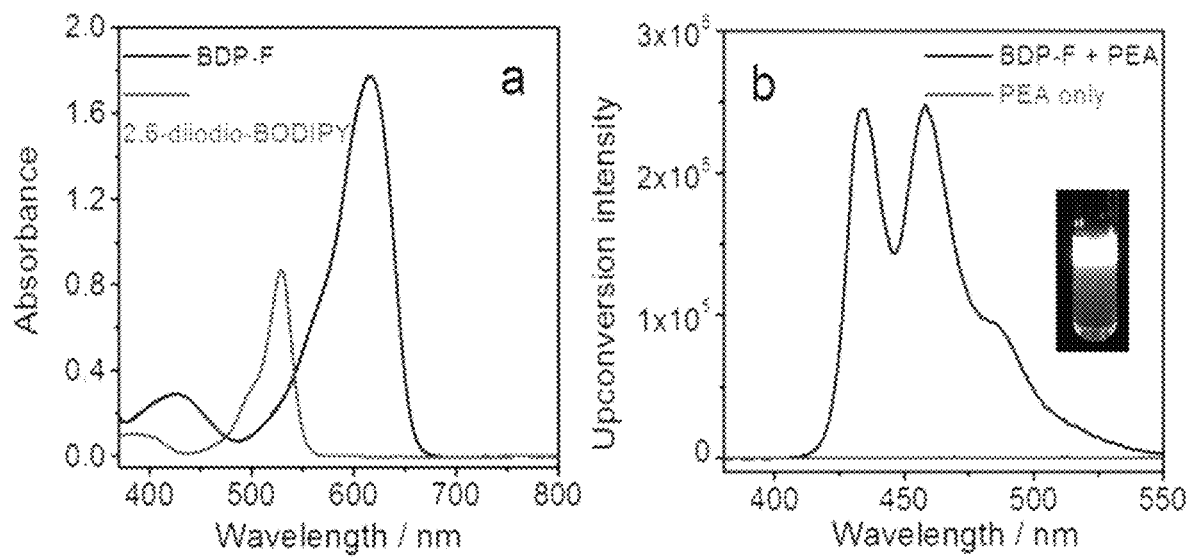
FIG. 1. (a) UV-vis absorption spectra of BDP-F and 2,6-diiodio-BODIPY (10 μM) in toluene at room temperature. (b) The upconversion emission spectra of BDP-F (20 μM) and PEA (0.2 mM) in a degassed toluene, $\lambda_{ex}$=650 nm (100 mW/cm²), inset shows such TTA-UC can be observed by the naked eye.

The invention is based in part on the unexpected discovery of a novel class of nano-materials characterized by triplet-triplet annihilation upconversion (TTA-UC), and compositions and methods of preparation thereof. The invention additionally provides method for using such materials and nanoparticles thereof for stimulus-responsive, in situ delivery of biologically active agents for a wide range of clinical applications.

The disclosed strategy of metal-free triplet-triplet annihilation unconventional expands anti-Stokes shifting from the far red to deep blue region, which is utilized in in vivo photorelease of a therapeutic agent (e.g., an anticancer prodrug). The triplet-triplet annihilation upconversion strategy demonstrated herein affords robust brightness and the record longest anti-Stokes shift from far red to deep blue. In addition, TTA nanocapsules (e.g., core-shell structured) for photo-triggered prodrug release provided herein operates with a low-power density, far red LED light (650 nm) and shows effective and efficient prodrug activation control and potent tumor-growth inhibition in vivo.

Due to its unique spatio-temporal control ability, photo-uncaging has recently been studied for disease therapy. Usually, photo-uncaging reaction depends on UV and deep blue light irradiation. However, the short wavelength light is limited in biological application due to high phototoxicity for cells and tissue and shallow tissue penetration. Photo-uncage reagents generally require two-photon near infrared excitations from pulse lasers to simulate UV and deep blue radiation, making such a process very expensive.

While rare earth-doped inorganic UCNPs have realized photo-uncaging with near infrared light irradiation (980 nm or 800 nm), major challenges remain in regard to inorganic UCNPs. For instance, due to the intrinsic low absorption and emission cross-sections of the contained lanthanide ions, such UCNPs have very low quantum yields and generally require high power density laser excitation. In addition, the long-term in vivo toxicity and systematic clearance of inorganic lanthanide ions inside UCNPs are also unclear.

Green to blue TTA-UC nanomicelles were recently reported to trigger the uncaging of blue light sensitive coumarin group modified peptides, thus enabling better subsequent cell targeting. (Wang, et al. *Nano Lett.* 2015, 15, 6332-6338.) However, in vivo drug photorelease and concomitant cancer treatment have been formidable challenges because the green excitation source lacks deep issue penetration depth and yields low quantum efficiency. Moreover, such TTA-UC remains insufficient to activate large amount of prodrug molecules for cancer treatment. (Lin, et al. 2010 *J. Am. Chem. Soc.* 132, 10645-10647.) To address this problem, certain deep tissue penetrable longer wavelength light excitable TTA system were proposed. For example, a TTA system containing meso-tetraphenyl-tetrabenzoporphine palladium PdTPBP (sensitizer) and perylene (emitter) can upconvert 635 nm laser light to 475 nm photons and was used for the photodissociation of ruthenium polypyridyl complexes from PEGylated liposomes in water. However, the existing system has limitations in biological in vivo applications due to its suboptimal efficiency and relatively high excitation power density (2.3 W/cm$^2$), which is beyond the biosafety threshold. (Askes, et al. 2014 *Angew. Chem. Int. Ed.,* 53, 1029-1033.) In addition, the anti-Stokes shifted emission wavelength of 475 nm is not compatible with the typical deep blue/UV operation wavelengths for biologically used caging groups. (Croissant, et al. 2013 *Angew. Chem. Int. Ed.* 52, 13813-13817; Fenno, et al. 2011 *Annu. Rev. Neurosci.* 34, 389-412; Huebsch, et al. 2014 *Proc. Natl. Acad. Sci. USA.* 111, 9762-9767.)

Herein disclosed is a metal-free, biocompatible upconversion strategy, in particular exploring organic chromophore-based TTA-UC. This strategy is demonstrated to expand anti-Stokes shifting from in the red region (from about 500 nm to about 600 nm) or far red region (from about 600 nm to about 700 nm) to the deep blue region (from about 410 to about 550 nm) in metal-free TTA-UC and is suitable for in vivo titrating anticancer prodrug photorelease.

As illustrated in Scheme 1a, low energy photons can be absorbed by a sensitizer chromophore and can then be transferred to an acceptor chromophore through a unique triplet-triplet energy transfer process. Two excited acceptor molecules subsequently underwent TTA annihilation process, generating one high-energy short wavelength photon.

Scheme 1

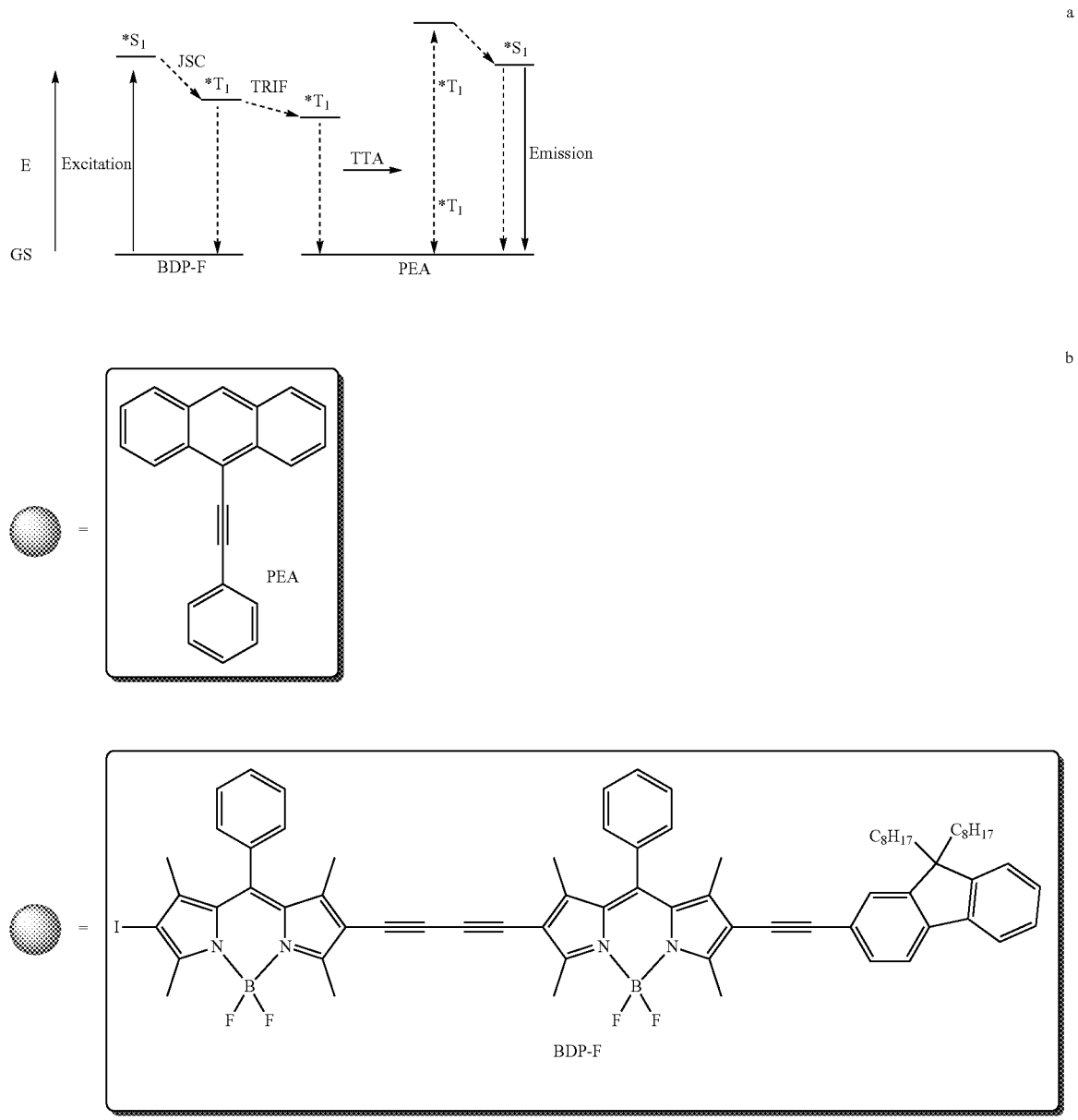

(a) A Jablonski diagram of the photophysical processes of the triplet photosensitizers and the TTA upconversion exemplified with BDP-F as the triplet photosesitizer and PEA as the emitter; (b) Molecular structure of BDP-F and PEA.

Benefiting from the robust brightness and long anti-Stokes shift, a novel TTA core-shell-structured prodrug delivery system is provided herein that can be operated with a low power density far red-LED light (650 nm). For example, the delivery system employs mesoporous silica nanoparticles preloaded with TTA molecules as the core and amphiphilic polymers encapsulating anti-cancer prodrug molecules as the shell. When stimulated by far red light (650 nm), the intense TTA upconversion blue emission activated the anticancer prodrug molecules and showed effective tumor growth inhibition in vivo. This invention paves the way for the use of organic TTA upconversion systems in various biophotonic applications with in vivo photo-controllable drug release.

Comparing to inorganic UCNPs, the TTA-UC system disclosed herein offers significant advantages due to its intense absorption coefficient of sensitizers, high quantum yield and brightness, as well as the concomitant low power density excitation resource. (Singh-Rachford, et al. *Coord. Chem. Rev.* 2010, 254, 2560-2573; Zhao, et al. *RSC. Adv.* 2011, 1, 937-950; Zhao, et al. *Chem. Soc. Rev.* 2013, 42, 5323-5351; Zhao, et al. *Chem. Soc. Rev.* 2015, 44, 8904-8939; Zhou, et al. *Chem. Rev.* 2015, 115, 395-465.)

The TTA-UC system possesses dramatically improved anti-Stokes shift, coupled with highly desirable robust brightness and biocompatibility, allowing the present system to be applicable in various applications as photo-controllable drug delivery systems.

In addition, novel photosensitizers and emitters are employed, which together achieve large antistokes shift from far red or near infrared (NIR) excitation to deep-blue emission with low power intensity excitation.

Scheme 2

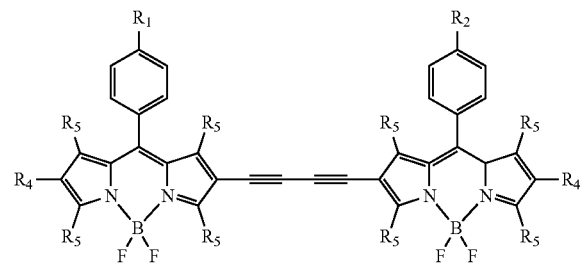

Molecular structure of photosensitizer~BDP-F substituted functional groups (R's as defined herein).

Thus, in one aspect, the invention generally relates to an upconversion composition, comprising an organic triplet photosensitizer molecule and an organic emitter molecule, wherein the composition is characterized by an upconversion upon excitation in the red region of about 500 nm to about 600 nm or far red region of about 600 nm to about 700 nm with an emission in the deep blue region of about 410 nm to about 550 nm, wherein each of the triplet photosensitizer and emitter molecules comprises no metallic elements.

In certain embodiments of the composition, the emitter molecule is 9-phenylacetylene anthracene or a derivative thereof.

In certain embodiments, excitation is in the region of about 500 nm to about 550 nm, about 550 nm to about 600 nm, about 600 nm to about 650 nm, or about 650 nm to about 700 nm.

In certain embodiments, emission in the region of about 410 nm to about 450 nm, about 450 nm to about 500 nm, about 500 nm about 550 nm.

In certain embodiments of the composition, the triplet photosensitizer molecule is boron-dipyrromethene (BODIPY) dimer or a derivative thereof.

In certain embodiments of the composition, the triplet photosensitizer molecule is boron-dipyrromethene (BODIPY) dimer.

In certain embodiments of the composition, the triplet photosensitizer molecule has the structural formula (I):

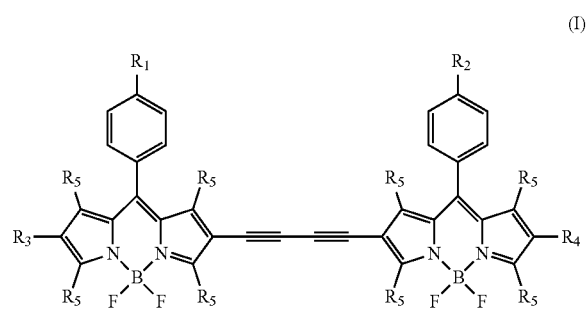

wherein
each of $R_1$ and $R_2$ is independently selected from the group consisting of: H, bromo, iodio, alkynyl, alkyl, alkenyl, azide, PEG, amino, carboxyl acid and hydroxyl;

$R_3$ is selected from the group consisting of: bromo and iodio;

$R_4$ is an arylethynyl group; and each $R_5$ is independently selected from the group consisting of: H and alkyl.

In certain embodiments of the composition, $R_4$ is selected from the group consisting of: phenylethynyl, naphthalene ethynyl, carbazole ethynyl and fluorenyl ethynyl.

In certain embodiments of the composition, $R_4$ is selected from the group consisting of:

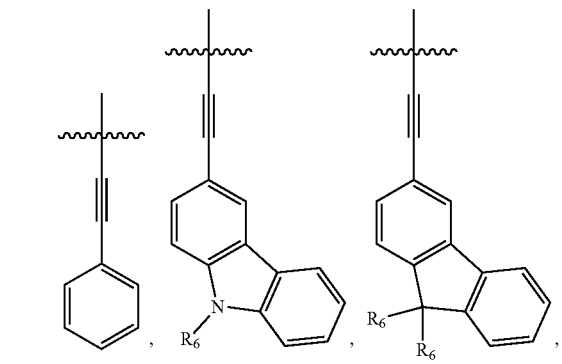

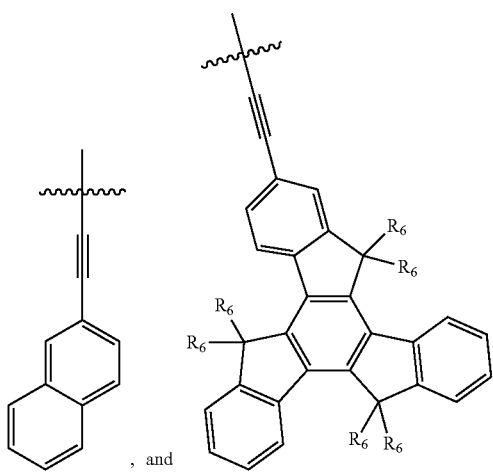

wherein each $R_6$ is independently a $C_2$-$C_{16}$ (e.g., $C_{12}H_{25}$) alkyl group.

Any suitable molar ratios of triplet photosensitizer:emitter may be employed, e.g., from about 1:1 to about 1:5, from about 1:5 to about 1:10, from about 1:10 to about 1:100.

In certain embodiments, the composition further includes an unsaturated olefin (e.g., those listed in Scheme 3).

Scheme 3.
Molecular structure of oleic acid derivatives for preventing oxygen quenching TTA-UC.

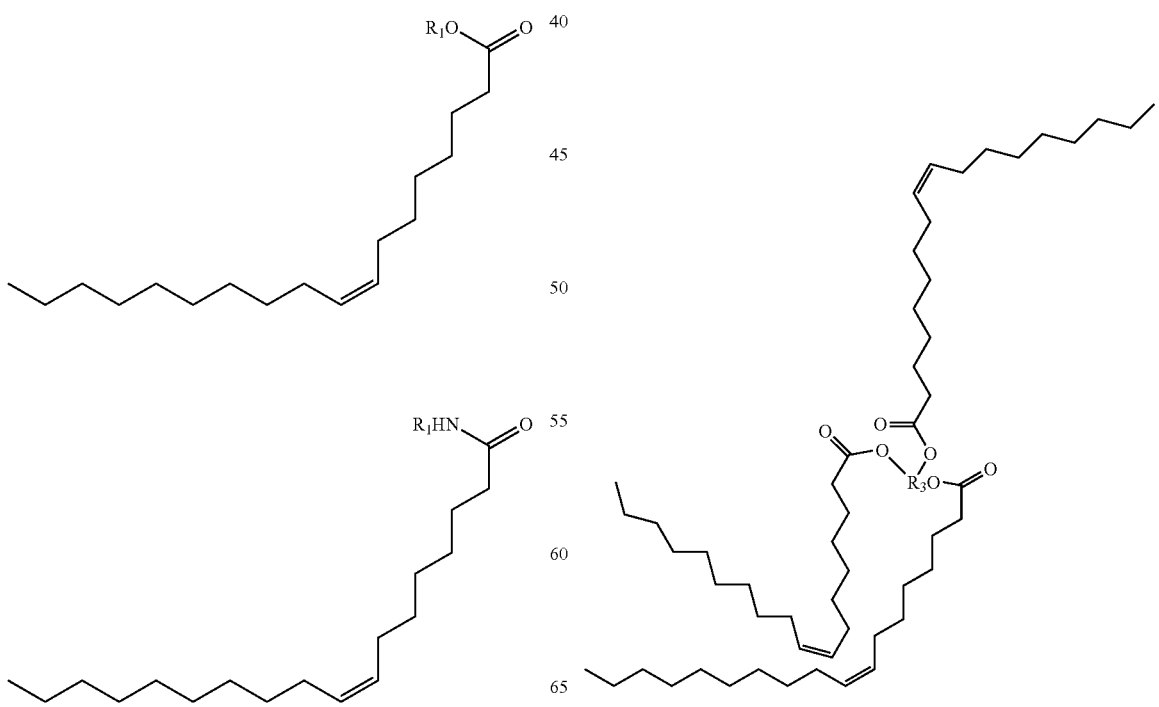

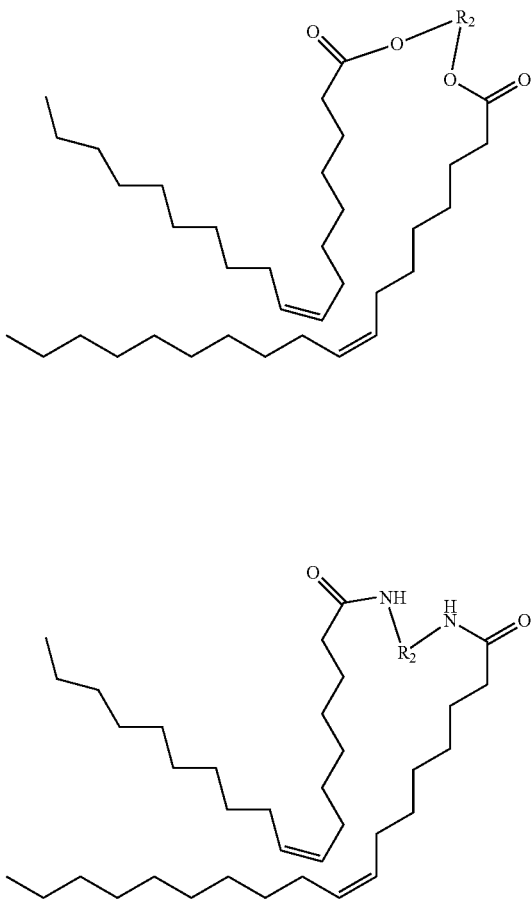

-continued

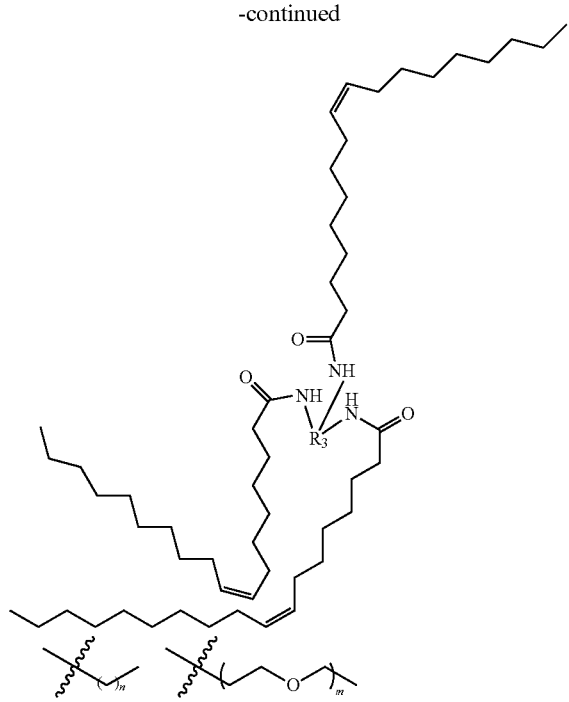

$R_1$ = $C_1$ to $C_{18}$ alkane (n < 18), PEG (molelar weight < 2000),

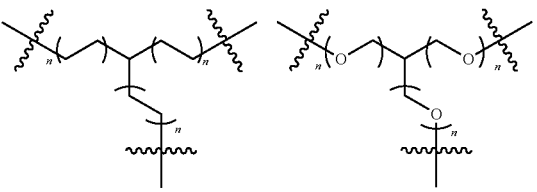

$R_2$ = $C_1$ to $C_{18}$ alkane (n < 18), PEG (molelar weight < 2000),

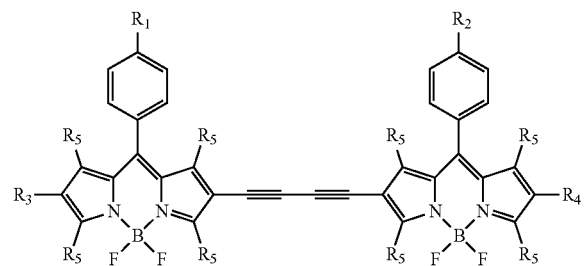

$R_3$ = $C_1$ to $C_{18}$ alkane (n < 18), PEG (molelar weight < 2000),

Molecular structure of oleic acid derivatives for preventing oxygen quenching TTA-UC.

In another aspect, the invention generally relates to a compound having the structural formula (I):

![formula I]

(I)

wherein each of $R_1$ and $R_2$ is independently selected from the group consisting of: H, bromo, iodio, alkynyl, alkyl, alkenyl, azide, PEG, amino, carboxyl acid and hydroxyl;

$R_3$ is selected from the group consisting of: bromo and iodio;

$R_4$ is an arylethynyl group; and each $R_5$ is independently selected from the group consisting of: H and alkyl.

In certain embodiments of the compound, $R_4$ is selected from the group consisting of: phenylethynyl, naphthalene ethynyl, carbazole ethynyl and fluorenyl ethynyl.

In certain embodiments of the compound, $R_4$ is selected from the group consisting of:

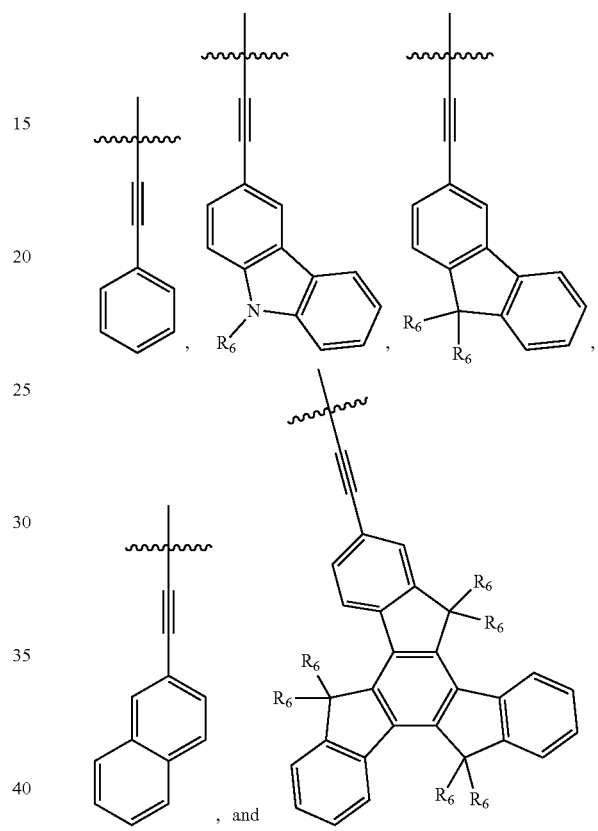

, and wherein each $R_6$ is independently a $C_2$-$C_{16}$ (e.g., $C_{12}H_{25}$) alkyl group.

In certain embodiments of the compound, each of $R_1$ and $R_2$ is H, $R_3$ is I, $R_4$ is a substituted or unsubstituted fluorenyl ethynyl, and each $R_5$ is methyl.

In yet another aspect, the invention generally relates to a biocompatible nanoparticle delivery system. The system includes: a triplet photosensitizer molecule and an emitter molecule, wherein each of the triplet photosensitizer and emitter molecules is an organic molecule and comprises no metallic elements; the triplet photosensitizer is excited by a light in the red region of about 500 nm to about 600 nm or far red region of about 600 nm to about 700 nm causing an emission by the emitter molecule in the deep blue region of about 410 nm to about 500 nm; and a photolabile molecule comprising a biologically active agent, wherein the biologically active agent is releasable upon absorption of the emission by the emitter molecule.

In certain embodiments, excitation is in the region of about 500 nm to about 550 nm, about 550 nm to about 600 nm, about 600 nm to about 650 nm, or about 650 nm to about 700 nm.

In certain embodiments, emission in the region of about 410 nm to about 450 nm, about 450 nm to about 500 nm, about 500 nm about 550 nm.

In certain embodiments of the system, the nanoparticle is characterized by a core-shell structure, wherein the triplet photosensitizer molecule and an emitter molecule are deposed in the core whereas the photolabile molecule is deposed in the shell.

In certain embodiments of the system, the emitter molecule is 9-phenylacetylene anthracene.

In certain embodiments of the system, the triplet photosensitizer molecule is boron-dipyrromethene (BODIPY) dimer, or a derivative thereof.

In certain embodiments of the system, the triplet photosensitizer molecule has the structural formula (I):

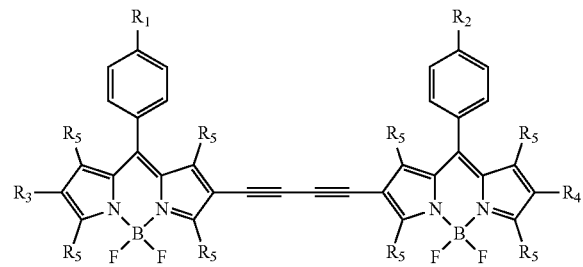

(I)

wherein each of $R_1$ and $R_2$ is independently selected from the group consisting of: H, bromo, iodio, alkynyl, alkyl, alkenyl, azide, PEG, amino, carboxyl acid and hydroxyl;

$R_3$ is selected from the group consisting of: bromo and iodio;

$R_4$ is an arylethynyl group; and each $R_5$ is independently selected from the group consisting of: H and alkyl.

In certain embodiments of the system, $R_4$ is selected from the group consisting of: phenylethynyl, naphthalene ethynyl, carbazole ethynyl and fluorenyl ethynyl.

In certain embodiments of the system, $R_4$ is selected from the group consisting of:

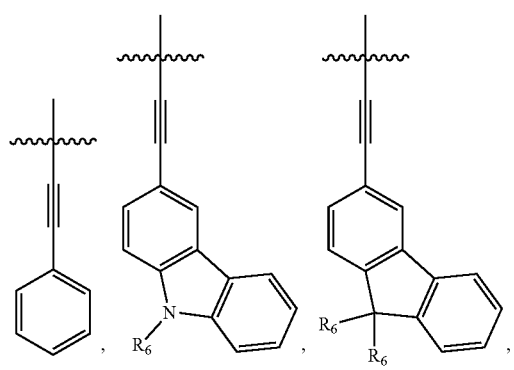

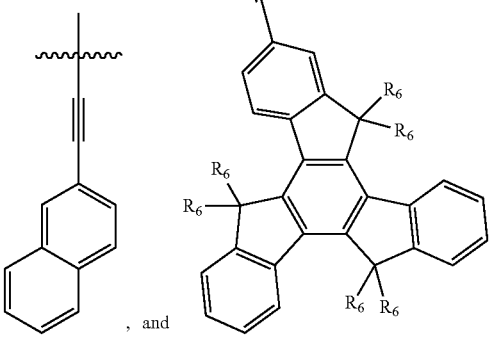

, and wherein each $R_6$ is independently a $C_2$-$C_{16}$ (e.g., $C_{12}H_{25}$) alkyl group.

Any suitable molar ratios of triplet photosensitizer:emitter may be employed, e.g., from about 1:1 to about 1:5, from about 1:5 to about 1:10, from about 1:10 to about 1:100.

In certain embodiments of the system, the biologically active agent is an anti-cancer agent.

In certain embodiments of the system, the photolabile molecule comprises a coumarin moiety.

In certain embodiments of the system, the anti-cancer agent is chlorambucil.

In certain embodiments, the system further includes an unsaturated olefin (e.g., those listed in Scheme 3).

In yet another aspect, the invention generally relates to a pharmaceutical composition comprising a nanoparticle delivery system or the compound disclosed herein.

In yet another aspect, the invention generally relates to a method for delivery of a bioactive agent to a target site. The method includes: administering to a subject in need thereof a biocompatible nanoparticle comprising: a triplet photosensitizer molecule and an emitter molecule, wherein each of the triplet photosensitizer and emitter molecules is an organic molecule and comprises no metallic elements; the triplet photosensitizer is excited by a light in the red region of about 500 nm to about 600 nm or far red region of about 600 nm to about 700 nm causing an emission by the emitter molecule in the deep blue region of about 410 nm to about 500 nm; and a photolabile molecule comprising a biologically active agent, wherein the biologically active agent is releasable upon absorption of the emission by the emitter molecule, and irradiating the target site with a light beam in the red region of about 500 nm to about 600 nm or far red region of about 600 nm to about 700 nm, thereby causing the release of the biologically active agent at the target site.

In certain embodiments, excitation is in the region of about 500 nm to about 550 nm, about 550 nm to about 600 nm, about 600 nm to about 650 nm, or about 650 nm to about 700 nm.

In certain embodiments, emission in the region of about 410 nm to about 450 nm, about 450 nm to about 500 nm, about 500 nm about 550 nm.

In yet another aspect, the invention generally relates to a method for treating tumor or cancer. The method includes: administering to a subject in need thereof a biocompatible nanoparticle comprising: a triplet photosensitizer molecule and an emitter molecule, wherein each of the triplet photosensitizer and emitter molecules is an organic molecule and comprises no metallic elements; the triplet photosensitizer is excited by a light in the red region of about 500 nm to about 600 nm or far red region of about 600 nm to about 700 nm causing an emission by the emitter molecule in the deep blue region of about 410 nm to about 550 nm; and a photolabile molecule comprising an antitumor or anticancer agent, wherein the antitumor or anticancer is releasable upon absorption of the emission by the emitter molecule, and irradiating the target site with a light beam in the red region of about 500 nm to about 600 nm or far red region of about 600 nm to about 700 nm, thereby causing the release of the antitumor or anticancer agent at the target site.

In certain embodiments, excitation is in the region of about 500 nm to about 550 nm, about 550 nm to about 600 nm, about 600 nm to about 650 nm, or about 650 nm to about 700 nm.

In certain embodiments, emission in the region of about 410 nm to about 450 nm, about 450 nm to about 500 nm, about 500 nm about 550 nm.

In certain embodiments of the methods, the biologically active agent is an anti-cancer agent.

In certain embodiments of the methods, the photolabile molecule comprises a coumarin moiety.

In certain embodiments of the methods, the anti-cancer agent is chlorambucil.

In certain embodiments of the methods, the emitter molecule is 9-phenylacetylene anthracene.

In certain embodiments of the methods, the triplet photosensitizer molecule is boron-dipyrromethene (BODIPY) dimer or a derivative thereof. In certain embodiments of the methods, the triplet photosensitizer molecule is boron-dipyrromethene (BODIPY) dimer.

In certain embodiments of the methods, the triplet photosensitizer molecule has the structural formula (I):

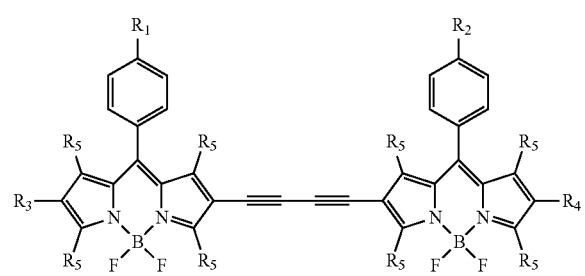

(I)

wherein
each of $R_1$ and $R_2$ is independently selected from the group consisting of: H, bromo, iodio, alkynyl, alkyl, alkenyl, azide, PEG, amino, carboxyl acid and hydroxyl;
$R_3$ is selected from the group consisting of: bromo and iodio;
$R_4$ is an arylethynyl group; and
each $R_5$ is independently selected from the group consisting of: H and alkyl.

In certain embodiments of the methods, $R_4$ is selected from the group consisting of: phenylethynyl, naphthalene ethynyl, carbazole ethynyl and fluorenyl ethynyl.

In certain embodiments of the methods, each of $R_1$ and $R_2$ is H, $R_3$ is I, $R_4$ is a substituted or unsubstituted fluorenyl ethynyl, and each $R_5$ is methyl.

In certain embodiments of the methods, $R_4$ is selected from the group consisting of:

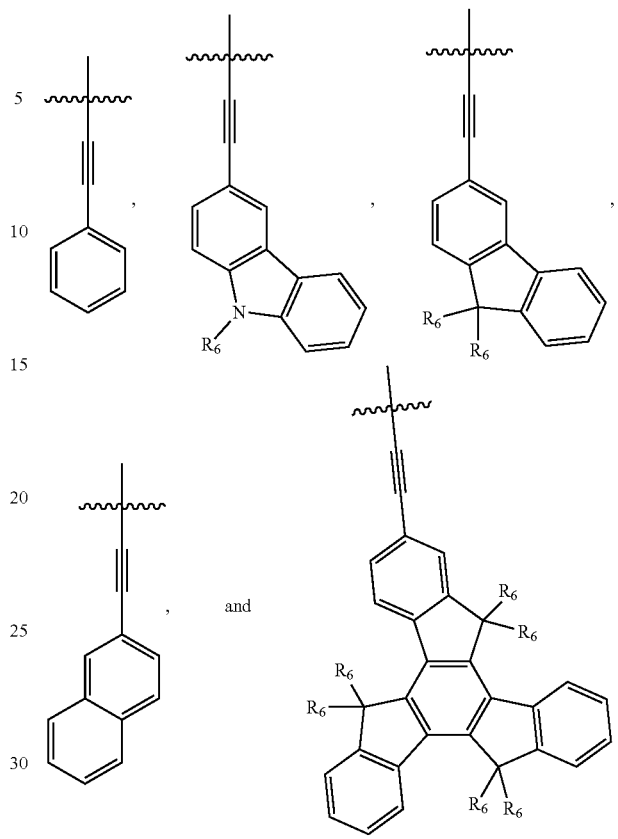

wherein each $R_6$ is independently a $C_2$-$C_{16}$ (e.g., $C_{12}H_{25}$) alkyl group.

Any suitable molar ratios of triplet photosensitizer:emitter may be employed, e.g., from about 1:1 to about 1:5, from about 1:5 to about 1:10, from about 1:10 to about 1:100.

In certain embodiments of the methods, the biocompatible nanoparticle further includes an unsaturated olefin (e.g., those listed in Scheme 3).

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 20, 1 to 10, 1 to 8, 1 to 6, 1 to 3, 6-20, 9-20, 12-20, 15-20, or 10-15 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents (e.g., acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(═O)($R^a$)($R^a$), or —O—P(═O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein). In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

The herein disclosed organic TTA upconversion system not only offers a new nanoplatform for spatio-temporal controlled cancer therapy, but also has great potential for numerous photonic and biophotonic applications.

Examples

A TTA-UC system was synthesized having a far-red absorption photosensitizer-BDP-F and deep blue emitter-PEA. A metal-free iodized BODIPY dimer (BDP-F) molecule was used as a highly far red-sensitive photosensitizer and 9-phenylacetylene anthracene (PEA) as a deep blue emitter (Scheme 1b). Compared to conventional BODIPY photosensitizers, such as 2, 6-diiodo-BODIPY (ε=85 000 $M^{-1}$ $cm^{-1}$ at 525 nm, Scheme 5), due to the large π-core, BDP-F presented broader and more intense absorption in the far-red region from 600 to 670 nm (peaking at 615 nm, ε=1.77×10$^5$$M^{-1}$ $cm^{-1}$; FIG. 1a).

Figure 5:
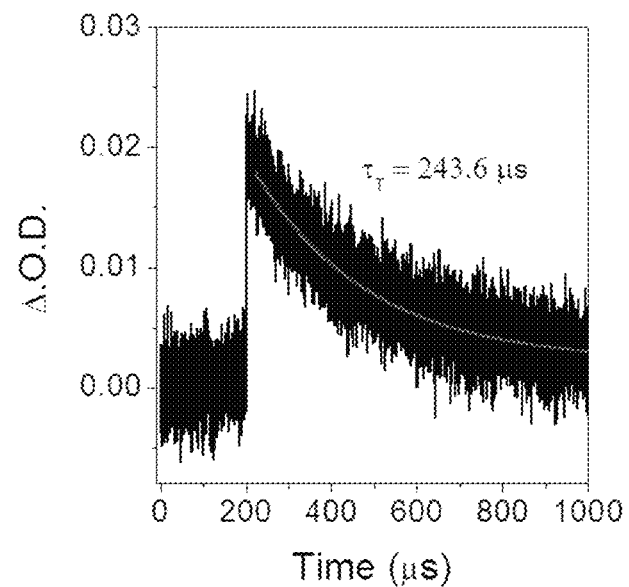
FIG. 5. Triplet excited lifetime spectra of BDP-F, 5 μM, in degassed toluene, $\lambda_{ex}$=610 nm.
Figure 6:
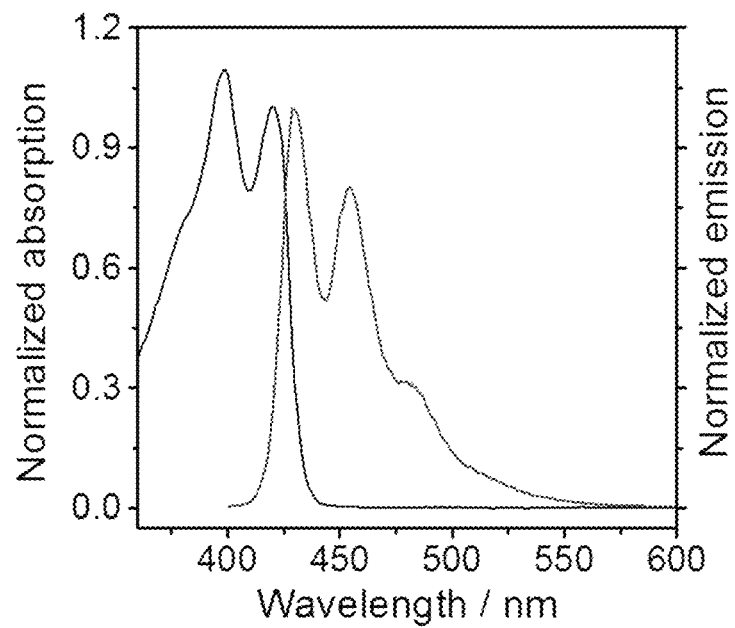
FIG. 6. Normalized absorption and normalized emission spectra of PEA in toluene, $\lambda_{ex}$, =390 nm.

Meanwhile, BDP-F has an outstanding triplet state lifetime ($\tau_T$=243.6 µs; FIG. 5) that is essential for the TTA photosensitizers. To increase the anti-Stokes shifted deep blue emission, 9-phenylacetylene anthracene (PEA) was synthesized as a new emitter (Scheme 4). Such PEA has presented excellent fluorescence quantum yield in the deep blue region from 410 to 500 nm, peaking at 432 nm ($\Phi_f$=87%; FIG. 6), making it particularly suitable to act as the emitter.

Figure 7:
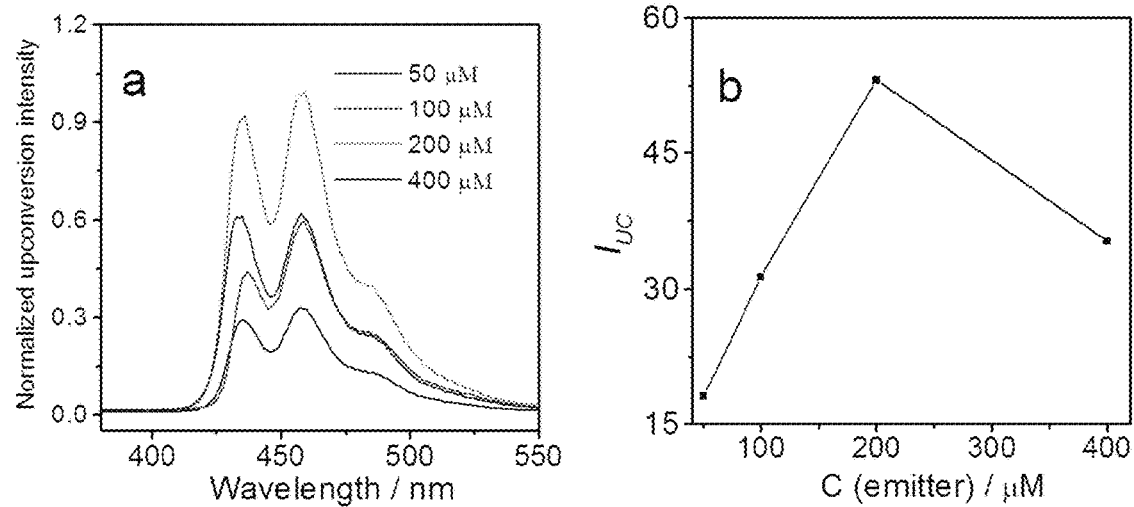
FIG. 7. (a) Upconversion emission spectra BDP-F (15 μM) and different concentration PEA in degassed toluene; (b) The integrated upconversion intensity of different concentration PEA. $\lambda_{ex}$=650 nm, 100 mW/cm².
Figure 8:
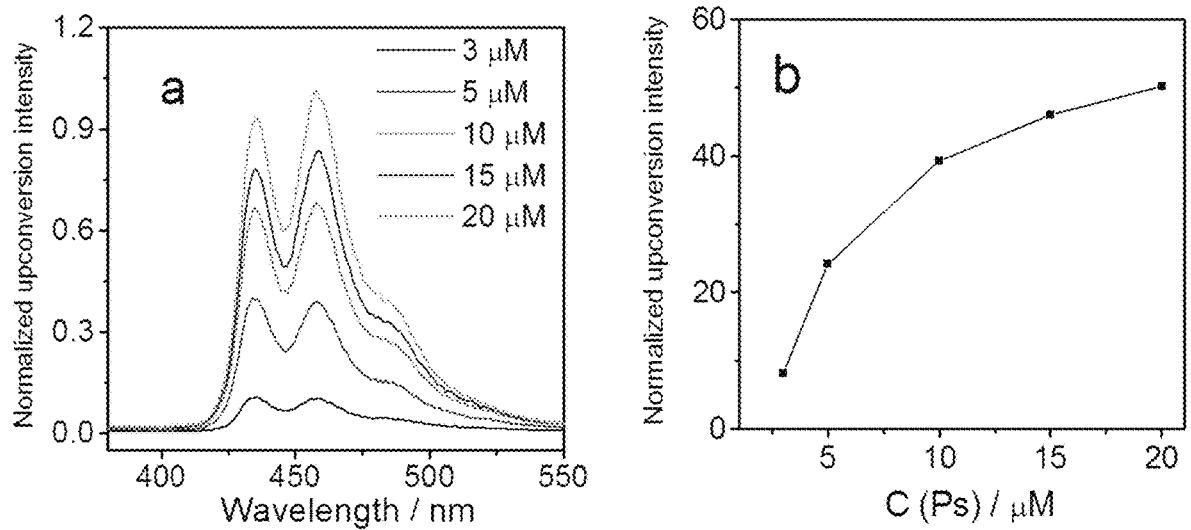
FIG. 8. (a) Upconversion emission spectra PEA (200 μM) and different concentration BDP-F in degassed toluene; (b) The integrated upconversion intensity of different concentration BDP-F $\lambda_{ex}$=650 nm, 100 mW/cm².

Further optimized was the concentration ratio of BDP-F and PEA in the TTA-UC system. It was found that their best combination was at 20 µM for BDP-F and 200 µM for PEA in degassed toluene solution (FIGS. 7-8). Under such an optimal ratio, intense deep blue emission in the range of 410-500 nm can be observed by the naked eye under the irradiation of 650 nm light (FIG. 1b). This TTA-UC system showed high a relative upconversion quantum yield ($\Phi_{UC}$=3.1%) by using methyl blue as a reference. The TTA-UC also presented excellent upconversion brightness ($\eta$=ε×$\Phi_{UC}$, 1054 at 100 mW/cm$^2$ of 650 nm).

Figure 9:
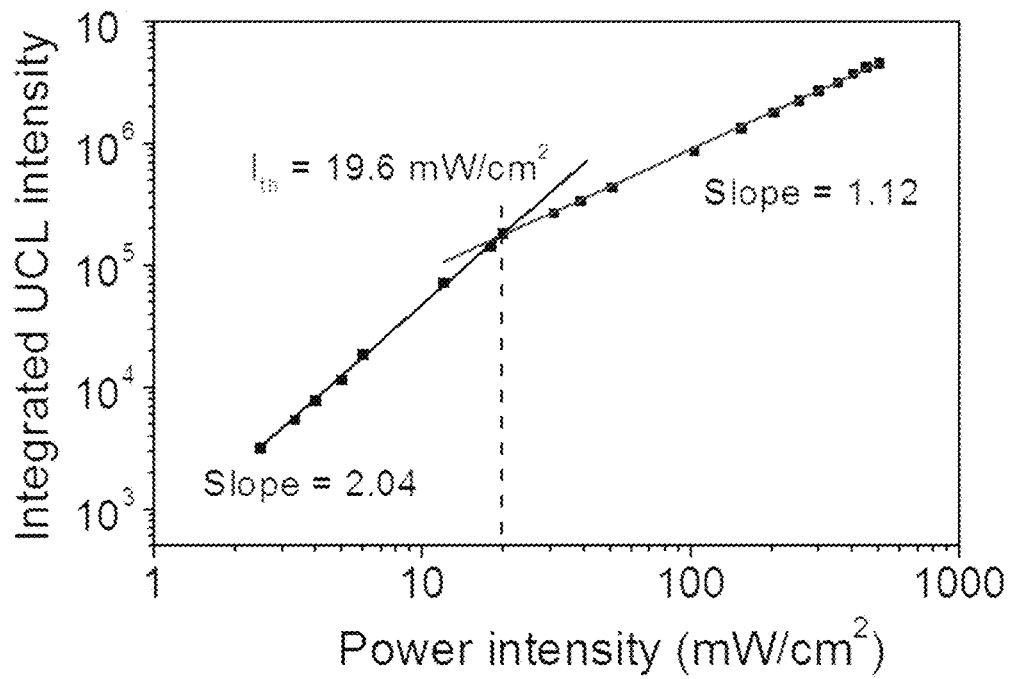
FIG. 9. Incident light power dependence study of TTA-upconversion for BDP-F (20 μM) and PEA (200 μM) in degassed toluene. Double-logarithmic plot of PEA integrated emission intensity as a function of 650 nm excitation power density. Solid lines illustrate a slope of 2.04 (black, quadratic) and a slope of 1.12 (red, linear). The transition threshold ($I_{th}$) between the quadratic and the linear regime occurs 19.6 mW cm⁻².

To the best of our knowledge, the TTA-UC system presents the longest anti-Stokes shift (Δλ=0.96 eV) among all the reported TTA upconversion systems (Table 1). Further, the TTA upconversion intensity threshold ($I_{th}$) was studied (FIG. 9). The quadratic dependence of the upconversion emission was indeed observed for low-energy incident power density excitation and the linear region observed at higher incident power densities in deaerated toluene. The transition threshold ($I_{th}$) between the quadratic and the linear regime occurs near 19.6 mW cm$^{-2}$, which is comparable to reported TTA-UC systems (Murakami, et al. 2016 *J. Phys. Chem. B* 120, 748-755). Power dependence experiment provides solid evidence for TTA-UC in BDP-F and PEA system in deaerated toluene. (Monguzzi, et al. 2008 *Phys. Rev. B.* 78, 195112).

TABLE 1

Comparison of previous reported TTA-UC systems and our new system

| Entry | Photosensitizers | Emitters | $\lambda_{ex}$ (nm) | $\lambda_{em}$ (nm) | Δλ (eV)$^m$ | $\Phi_{UC}$$^n$ | $\Phi_{UC}$$^o$ |
|---|---|---|---|---|---|---|---|
| 1$^a$ | PdTPBP | perylene | 635 nm (1.95 eV) | 470 nm (2.64 eV) | 0.69 eV | 7.2% | —$^p$ |
| 2$^b$ | PtTPBP | BODIPY | 635 nm (1.95 eV) | 528 nm (2.35 eV) | 0.40 eV | 3.1% | —$^p$ |
| 3$^b$ | PtTPBP | BODIPY | 635 nm (1.95 eV) | 546 nm (2.27 eV) | 0.32 eV | 7.5% | —$^p$ |
| 4$^c$ | PtTPBP | BDPPA | 635 nm (1.95 eV) | 470 nm (2.64 eV) | 0.69 eV | 9.3% | —$^p$ |
| 5$^d$ | Pyr$_1$RuPZn$_2$ | PDI | 780 nm (1.59 eV) | 541 nm (2.29 eV) | 0.70 eV | 0.75% | —$^p$ |
| 6$^e$ | Os complexes | rubrene | 938 nm (1.32 eV) | 570 nm (2.18 eV) | 0.86 eV | 3.1% (10 W/cm$^2$) | —$^p$ |
| 7$^f$ | PdPc(OBu)$_8$ | rubrene | 730 nm (1.69 eV) | 570 nm (2.17 eV) | 0.48 eV | —$^p$ | —$^p$ |
| 8$^g$ | 2I-BODIPY | perylene | 532 nm (2.33 eV) | 470 nm (2.63 eV) | 0.30 eV | 7.5% | —$^p$ |
| 9$^h$ | PtOEP | DPA | 532 nm (2.33 eV) | 430 nm (2.88 eV) | 0.50 eV | 23.2% | 4.5% |
| 10$^i$ | Trans-Pt(II)BDP | PDI | 635 nm (1.95 eV) | 541 nm (2.29 eV) | 0.35 eV | 7.0% | —$^p$ |
| 11$^j$ | Ruthenium(II) Polyimine Complexes | DPA | 532 nm (2.33 eV) | 400 nm (3.1 eV) | 0.77 eV | 9.8% | —$^p$ |
| 12$^k$ | Pt(II)BDP | perylene | 635 nm (1.95 eV) | 470 nm (2.64 eV) | 0.69 eV | 5.2% | —$^p$ |
| 13$^l$ | QDs (PbS) | rubrene | 850 nm (1.46 eV) | 580 nm (2.13 eV) | 0.68 eV | 1.2% | —$^p$ |

TABLE 1-continued

Comparison of previous reported TTA-UC systems and our new system

| Entry | Photosensitizers | Emitters | $\lambda_{ex}$ (nm) | $\lambda_{em}$ (nm) | $\Delta\lambda$ (eV)[m] | $\Phi_{UC}{}^n$ | $\Phi_{UC}{}^o$ |
|---|---|---|---|---|---|---|---|
| 14 | BDP-F | PEA | 650 nm (1.91 eV) | 432 nm (2.87 eV) | 0.96 eV | 3.1% | 2.0% |

[a] Ref. 5;
[b] Ref. 6;
[c] Ref. 7;
[d] Ref. 8;
[e] Ref. 9;
[f] Ref. 10;
[g] Ref. 11;
[h] Ref. 12;
[i] Ref. 13;
[j] Ref. 14;
[k] Ref. 15;
[l] Ref. 16;
[m] anti-Stokes shift;
[n] in the organic solvent;
[o] in the water;
[p] not reported.
(1) Wu, et al. *J. Org. Chem.*, 2011, 76, 7056-7064.
(2) Guo, et al. *J. Mater. Chem.* 2012, 22, 15757-15768.
(3) Lin, et al. *J. Am. Chem. Soc.* 2010, 132, 10645-10647.
(4) Zhao, et al. *Adv. Funct. Mater.* 2014, 24, 363-371.
(5) Cui, et al. *J. Org. Chem.* 2014, 79, 2038-2048.
(6) Singh-Rachford, et al. *J. Am. Chem. Soc.* 2008, 130, 16164-16165.
(7) Jiang, et al. *J. Am. Chem. Soc.* 2013, 135, 16446-16453.
(8) Singh-Rachford, et al. *J. Am. Chem. Soc.* 2010, 132, 14203-14211.
(9) Amemori, et al. *J. Am. Chem. Soc.* 2016, 138, 8702-8705.
(10) Duan, et al. *J. Am. Chem. Soc.* 2015, 137, 1887-1894.
(11) Zhang, et al. L. *J. Am. Chem. Soc.* 2013, 135, 10566-10578.
(12) Liu, et al. *J. Am. Chem. Soc.* 2012, 134, 5390-5397.
(13) Wu, et al. *J. Mater. Chem. C*, 2013, 1, 705-716.
(14) Ji, et al. *Angew. Chem. Int. Ed.* 2011, 50, 1626-1629.
(15) Wu, et al. *Chem. Eur. J.* 2012, 18, 1961-968.
(16) Wu, et al. *Nature Photonics*, 2016, 10, 31-34.

Figure 34:
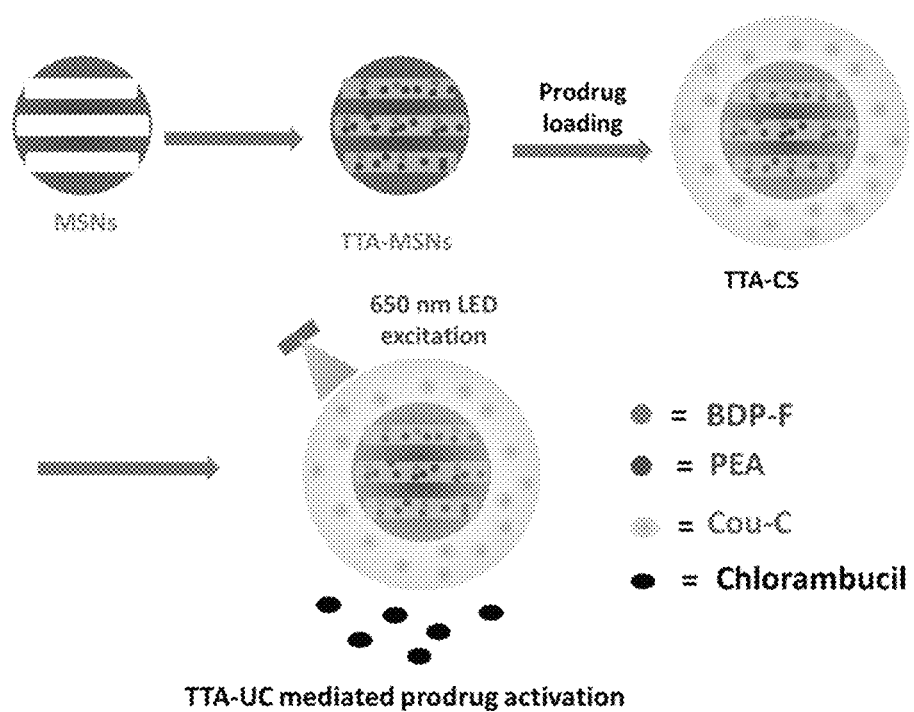
FIG. 34. Illustration of the preparation of TTA-CS, and TTA-UC mediated prodrug activation.

Due to such excellent photophysical properties, we then sought to construct a TTA-UC drug delivery system based on this new TTA system. In particular, we designed a TTA upconversion core/shell structured nanocapsule (TTA-CS). In the TTA-CS, TTA-MSNs as core structure are the TTA-UC nanoparticles with the TTA-UC dye pair, but without any photosensitive drug, while TTA-CS is the upconverting nanoparticles loaded with the deep blue light sensitive and hydrophobic prodrug (coumarin-chlorambucil (Cou-C), molecular structure FIG. 2) (Zhao, et al. 2014 *Adv. Funct. Mater.* 24, 363-371) (FIG. 34). After uncaging, the prodrug (Cou-C) is able to convert to hydrophilic chlorambucil which can release from TTA-CS and then kill the tumor cells.

An important finding was that a series of unsaturated olefins can efficiently prevent oxygen quenching to TTA-UC. For example, the following unsaturated olefins can efficiently prevent oxygen quenching the TTA-UC in the air.

Figure 10:
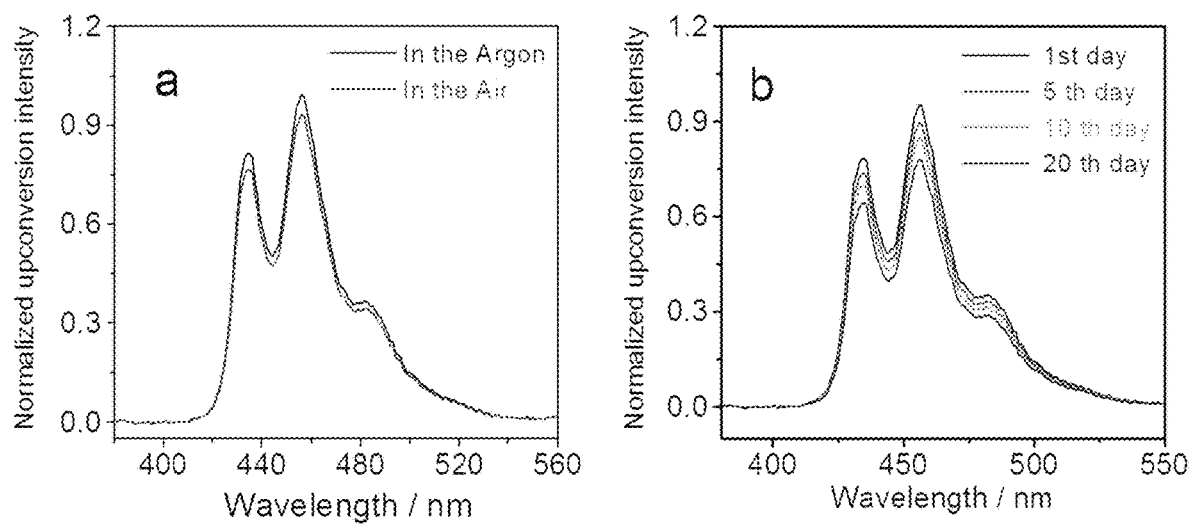
FIG. 10. (a) Normalized upconversion emission spectra of BDP-F (20 μM) and PEA (400 μM) in methyl oleate, in the argon and in the air condition; (b) Normalized upconversion emission spectra of BDP-F and PEA in different storage days (1, 5, 10, 20 day). $\lambda_{ex}$=650 nm, 100 mW/cm².

It was found that methyl oleate oil can efficiently prevent oxygen quenching to TTA-UC, as can be seen in FIG. 10a, Compared to in the argon condition, only 6% upconversion intensity reduced in the air. In addition, TTA-UC system of BDP-F and PEA in the methyl oleate was quite stable, even after 20 days, the upconversion emission intensity was reduced by only 9.0% in the present of air (FIG. 10b). And then, TTA-UC (20 μM of BDP-F and 200 μM of PEA) in methyl oleate oil was infused into mesoporous channels of silica nanoparticles to form TTA-MSNs.

Figure 11:
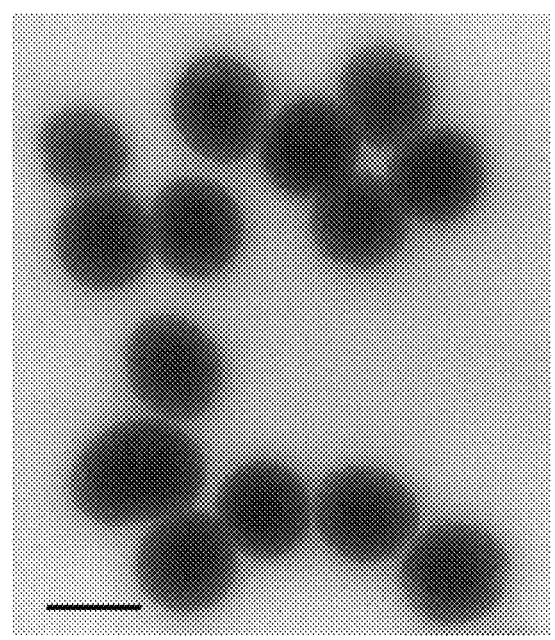
FIG. 11. TEM imaging of TTA-MSNs, scale bar 200 nm.
Figure 12:
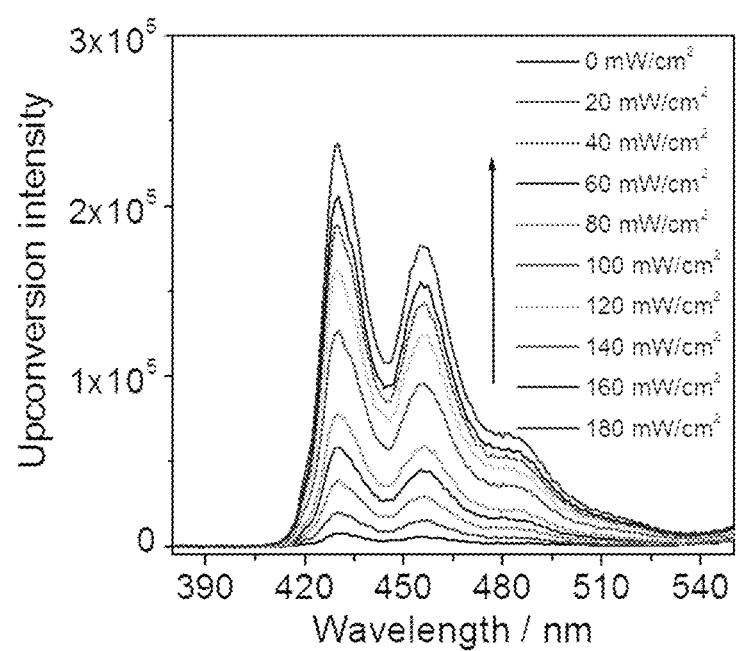
FIG. 12. Upconversion emission spectra of TTA-MSNs in different power intensity in PBS buffer in the air, 0.5 mg/mL, $\lambda_{ex}$=650 nm.
Figure 13:
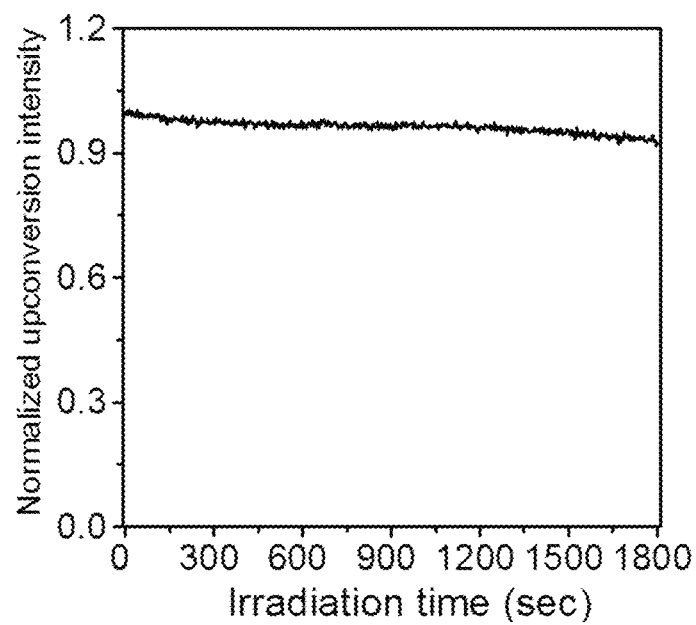
FIG. 13. Photostability of TTA-MSNs in PBS buffer, 0.5 mg/mL, $\lambda_{ex}$=650 nm, 100 mW/cm², in the air.

The TTA-MSNs were characterized by transmission electron microscopy (TEM). As shown in FIG. 11, the TEM image indicates that the TTA-MSNs consist of uniform spherical nanoparticles with a diameter of 218±16 nm. The hydrodynamic diameter is 259±12 nm as measured by the dynamic light scatter technique (DLS) in DI water. As shown in FIG. 12, upon 650 nm light excitation, TTA-MSNs generated a deep bright blue upconversion emission that peaks at 430 nm. Using methyl blue as the reference, the upconversion quantum yield ($\Phi_{UC}$) of TTA-MSNs in water was measured to be 2.0% (100 mW cm$^{-2}$) in the air. In addition, the photostability of TTA-MSNs was also investigated in the air. No significant changes in the TTA-UC were observed when TTA-MSNs were continuously irradiated by the 650 nm laser (100 mW cm$^{-2}$) for 30 min. (FIG. 13). This indicates the excellent photostability of TTA-MSNs.

Secondly, as shown in FIG. 34, TTA-CS was prepared by deep blue light sensitive hydrophobic prodrug (Zhao, et al. 2014 *Adv. Funct. Mater.* 24, 363-371) and TTA-MSNs co-encapsulated with amphiphilic polymer F-127 (TTA-CS). In TTA-CS, Chlorambucil was chosen because it has been reported to be a potent and cost-effective small molecule tumor inhibitor (Lin et al. 2010 *J. Am. Chem. Soc.* 132, 10645-10647; Zhao, et al. 2014 *Adv. Funct. Mater.* 24, 363-371.)

Figure 14:
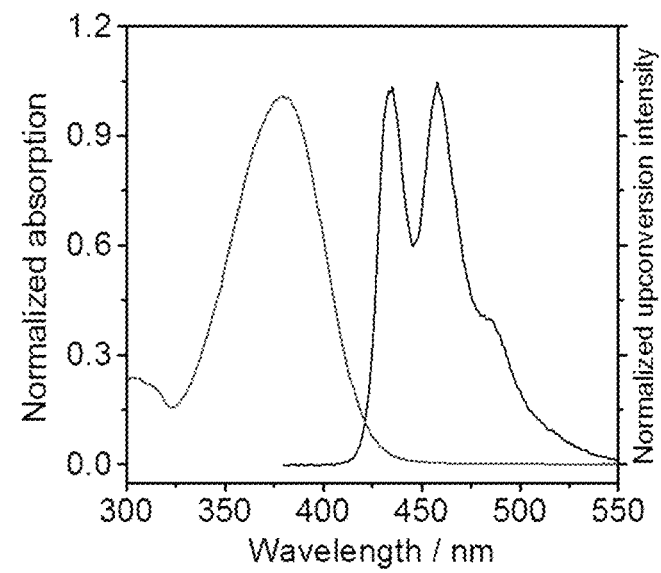
FIG. 14. Overlay normalized absorption spectra of Cou-C and normalized upconversion spectra of TTA-MSNs.
Figure 15:
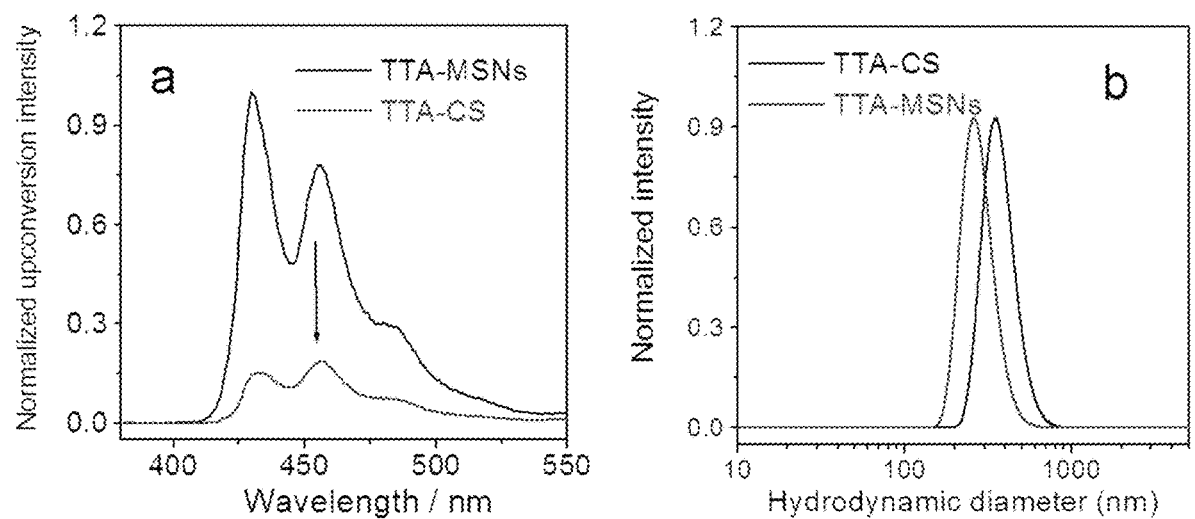
FIG. 15. (a) Upconversion emission spectra of TTA-MSNs and TTA-CS in PBS, in the air, $\lambda_{ex}$=650 nm, power intensity (100 mW/cm$^2$); (b) Hydrodynamic diameter of TTA-MSNs and TTA-CS in DI water, laser wavelength 633 nm.
Figure 16:
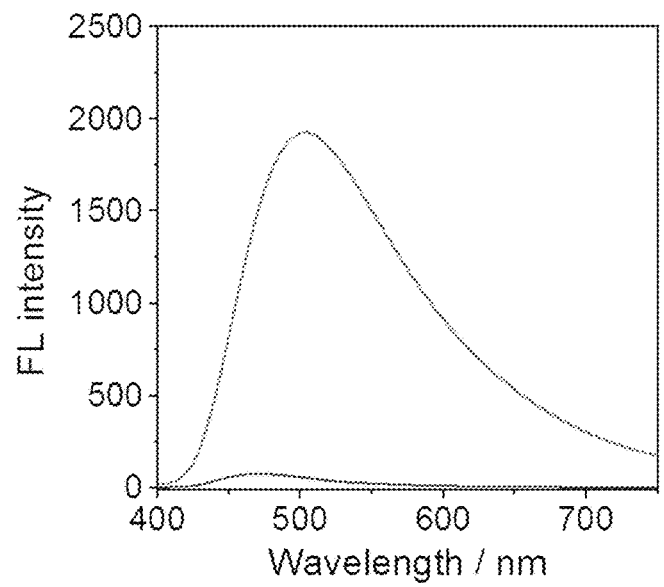
FIG. 16. Fluorescence emission spectra of initially TTA-CS solution (green) and solution outside the cup (red), $\lambda_{ex}$=380 nm. The stability of the prodrug entrapment was further evaluated by dialyzing the TTA-CS in a Slide-A-Lyzer MINI dialysis cup (MWCO10,000) against PBS buffer for 24 h. The fluorescence of coumarin in the aqueous solution outside the dialysis cup was then measured. The fluorescence emission of initially TTA-CS solution located at 500 nm. When prodrug revealed from the shell of TTA-CS, the fluorescence emission of solution outside the cup blue-shifted to 470 nm after dialysis for 24 h, suggesting the prodrug coated on the shell of TTA-CS. The prodrug revealed proportion was calculated by following process: The intensity of initially TTA-CS is 1920 (a.u.), after the dialysis for 24 h, fluorescence spectra of the solution outside cup was tested, the intensity of solution outside cup is 79 (a.u.). The prodrug revealed proportion (%)=solution outside cup/initially TTA-CS solution intensity×100%. About 4.4% prodrug revealed from the dialysis bowl for 24 h.

Moreover, the coumarin-based group possesses high photocleavage efficiency and deep blue absorption wavelength, the latter of which overlaps with the emission spectrum of PEA (FIG. 14). As can be seen in FIG. 15a, the deep blue upconversion emission of the resulting TTA-CS is less than TTA-MSNs, suggesting that the prodrug (Cou-C) that absorbs the 430 nm light was successfully encapsulated within the system. The core/shell nanocapsule was further characterized by use of the DLS technique. The hydrodynamic diameter of the TTA-CS (358±27 nm) is larger than the diameter of TTA-MSNs (FIG. 15b), indicating that the presence of the amphiphilic polymer F-127 encapsulated prodrug is the external shell in the system. The prodrug entrapment efficiency was calculated by a previously reported method to be 79%. We found that the release of prodrug out of TTA-CSs in absence of 650 nm light is in fact rather insignificant (4.4% after 24 h). (FIG. 16).

Figure 2:
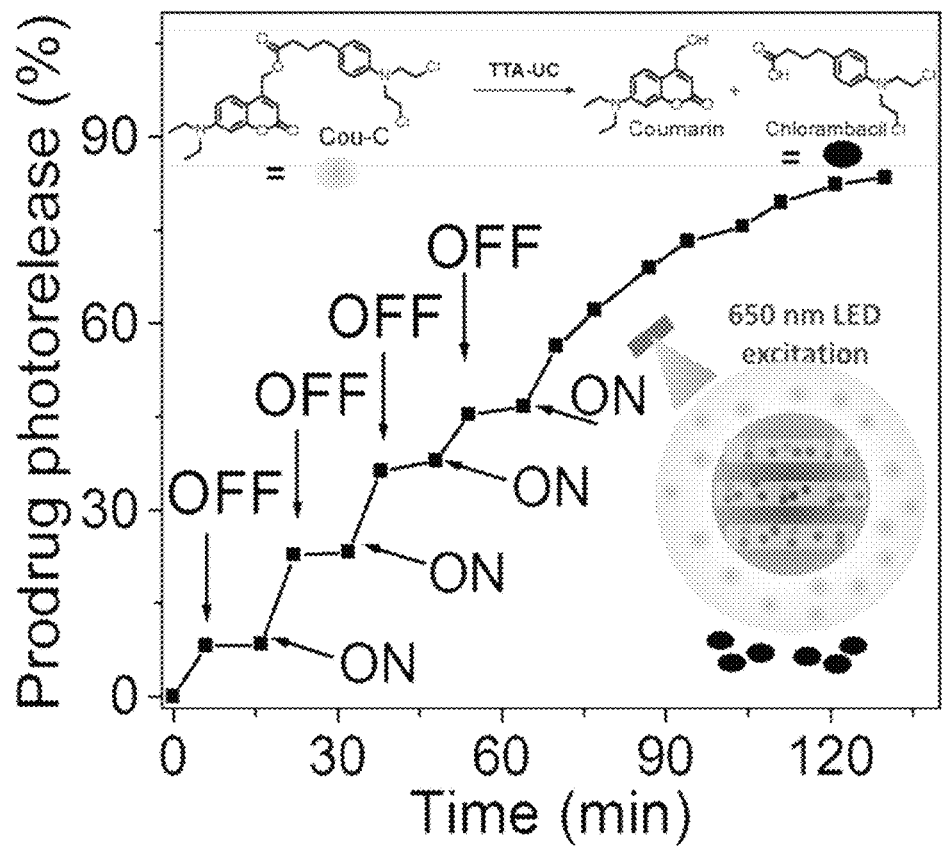
FIG. 2. The TTA-upconversion regulated activation of Cou-C from TTA-CS with a 650 nm LED irradiation. "ON" and "OFF" indicate the initiation and termination of LED irradiation, respectively, and the working power density was 100 mW cm⁻², top inset: the photoactivation reaction of Cou-C; bottom inset: schematic illustration of TTA-UC mediated prodrug activation process in TTA-CS.
Figure 17:
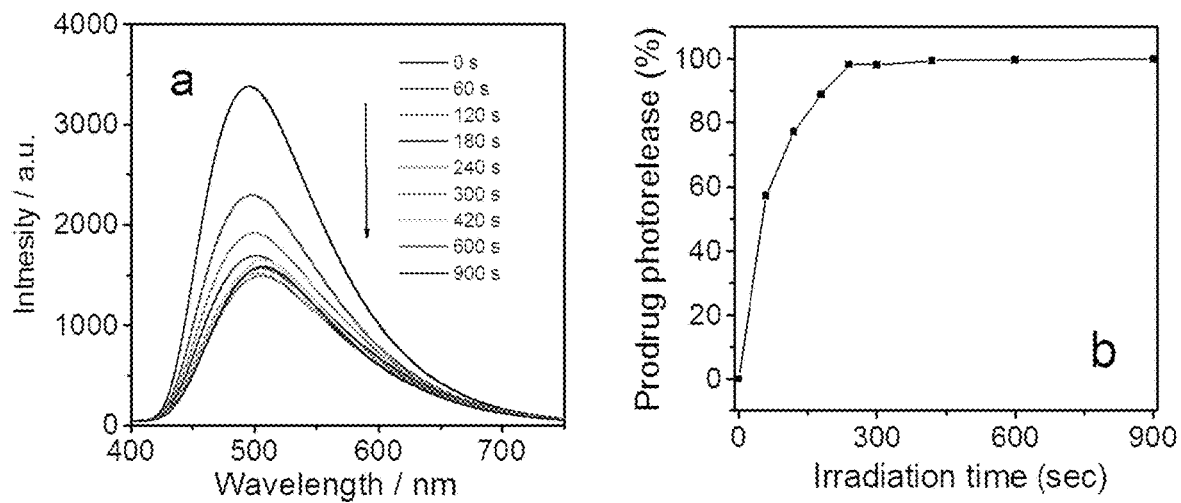
FIG. 17. (a) The change of fluorescence of Cou-C with UV light (365 nm) irradiation, $\lambda_{ex}$=390 nm; (b) UV light mediated prodrug photorelease process.
Figure 18:
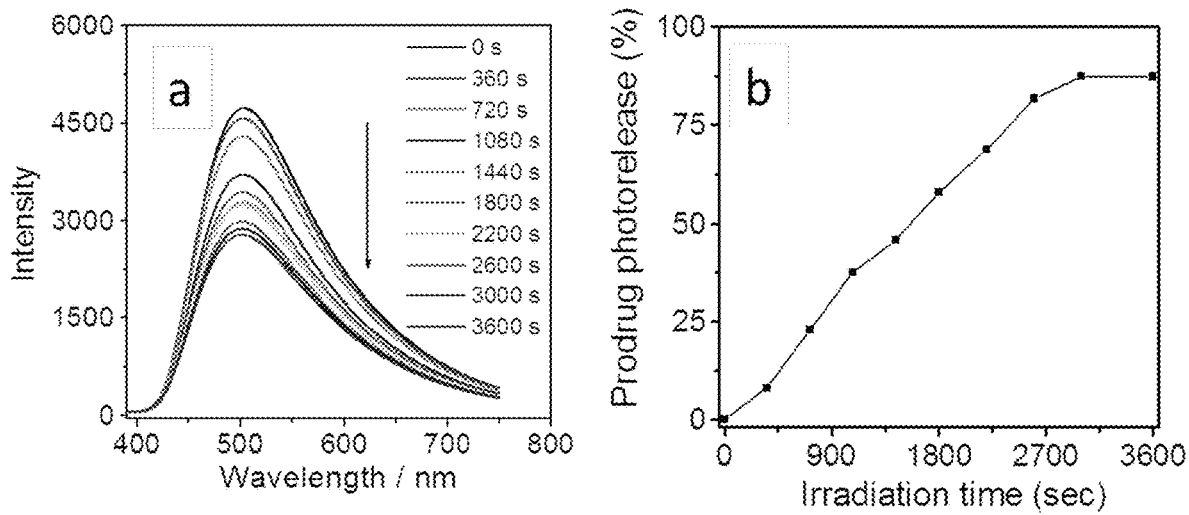
FIG. 18. (a) Time-dependent fluorescence spectra of the release chlorambacil under far red light LED irradiation (650 nm, 100 mW/cm$^2$) in TTA-CS; (b) The release profiles of chlorambucil from TTA-CS in PBS buffer with 650 nm LED irradiation, 100 mW/cm$^2$.

Next tested was the feasibility of prodrug activation using our TTA-CS system (FIG. 2). The activation of the prodrug process was quantified by the fluorescence measurement because the fluorescence of coumarin moiety at 498 nm decreases when it is removed from chlorambucil molecules (FIG. 17). As shown in FIG. 18, when we irradiated TTA-CS with 650 nm LED (100 mW/cm$^2$), the prodrug was uncaged, resulting in >48% activation of the prodrug within 30 min., and a maximum photorelease of ~82% of the prodrug after 60 min.

Figure 19:
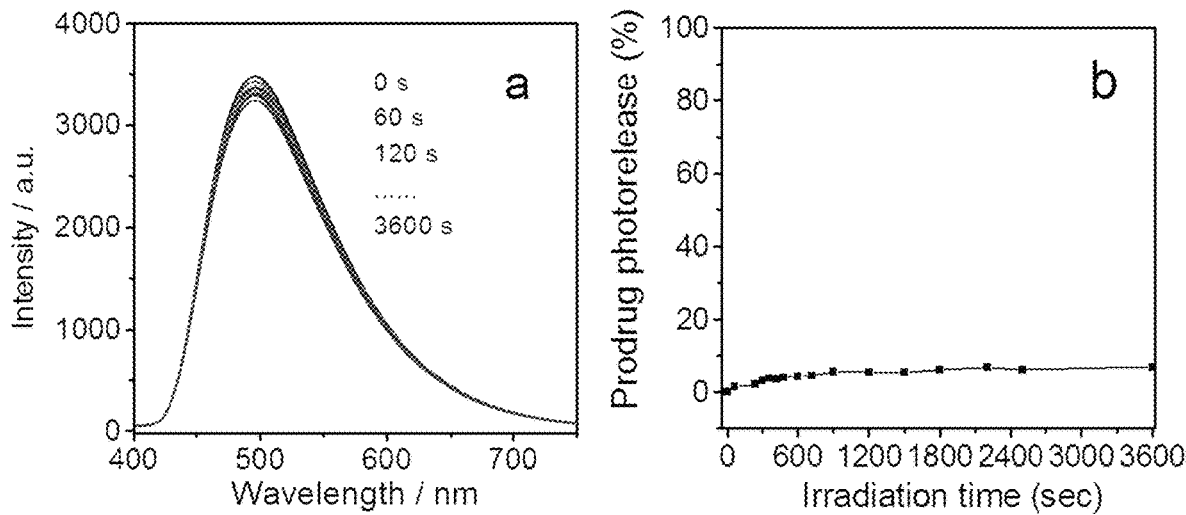
FIG. 19. (a) Time-dependent fluorescence spectra of the release chlorambacil under red light LED irradiation (650 nm, 100 mW/cm$^2$) in BDP-F-CS; (b) The release profiles of chlorambucil from BDP-F-CS in PBS buffer with 650 nm LED irradiation, 100 mW/cm$^2$.

These results confirmed that the prodrug can be activated by the TTA-upconversion process by far red light. As a control, a similar nanocapsule consisting of the photosensitizers without the PEA emitter (termed BDP-F-CS) was designed as a non-emissive control. Excluding the possibility of the direct uncaging of chlorambucil by 650 nm light (FIG. 19), upon 650 nm irradiation of BDP-F-CS for 60 min., no observable uncaged chlorambucil was detected. Moreover, the photorelease of chlorambucil was clearly dependent on the on-off pattern of the LED excitation source (FIG. 2). This indicates that the release dose and duration can be precisely titrated by far red light under a low power density of 100 mW cm$^{-2}$.

Figure 3:
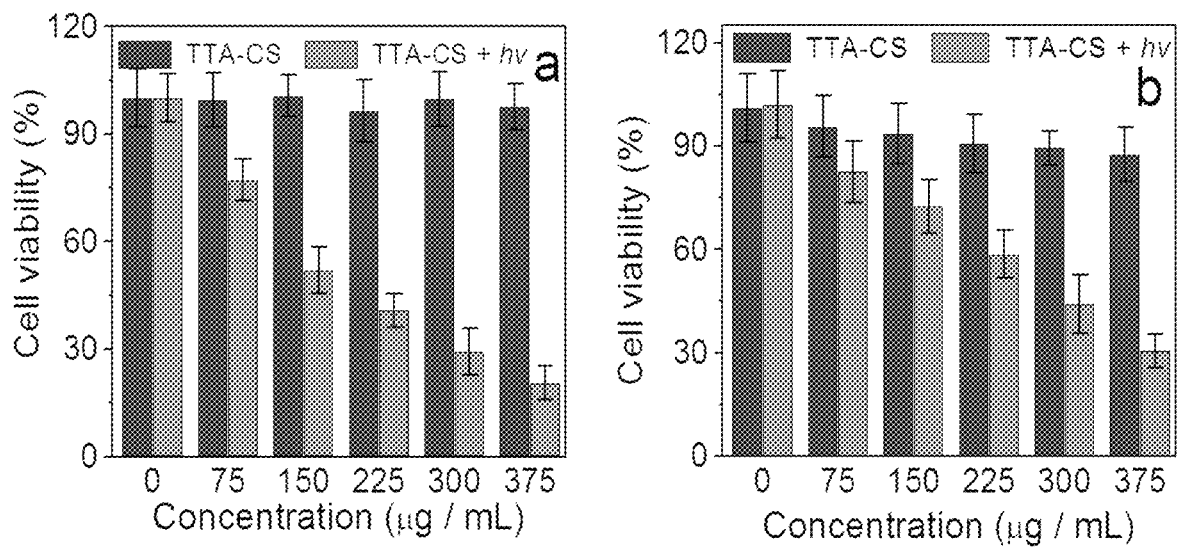
FIG. 3. MTT assay of Hela, $4T_1$ cell viability with different concentrations of TTA-CS with and without light. (a) Hela cells; (b) $4T_1$ cells. $\lambda_{ex}$=650 nm, photon fluence (360 J/cm²).
Figure 20:
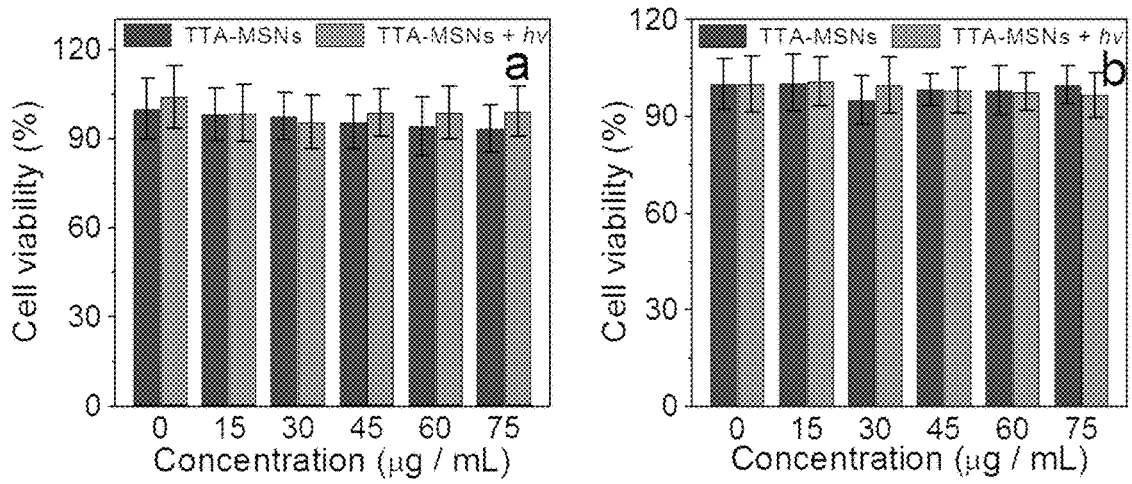
FIG. 20. MTT assay of Hela, 4T$_1$ cell viability with different concentrations of TTA-MSNs with and without light, (a) Hela cells; (b) 4T$_1$ cells. $\lambda_{ex}$=650 nm, photon fluence (360 J/cm$^2$).

To demonstrate in vitro effectiveness of our system, cell viability experiments were conducted. After the cancer cells (Hela and 4T1 cells) incubated with TTA-CS for 12 h, the low-power far-red LED was used. As shown in FIG. 20, TTA-MSNs have insignificant toxicity with and without light. In addition, TTA-CS presented negligible cell toxicity in the absence of LED light (the concentration range from 0 to 375 μg/mL). However, upon far red LED irradiation, TTA-CS presented significant cell toxicity for both Hela and 4T$_1$ cells, suggesting Cou-C is successfully photocleaved by TTA-UC and the hydrophilic anticancer chlorambucil is indeed released from TTA-CS into the cells, causing cancer cell death (FIG. 3). The IC$_{50}$ under light irradiation (half-maximal concentration of TTA-CS and Cou-C to cause cell death) was calculated to be 235±5.9 μg/mL and 2.74 μg/mL with Hela cells, 320±6.3 μg/mL and 3.64 μg/mL with 4T$_1$ cells respectively.

Figure 21:
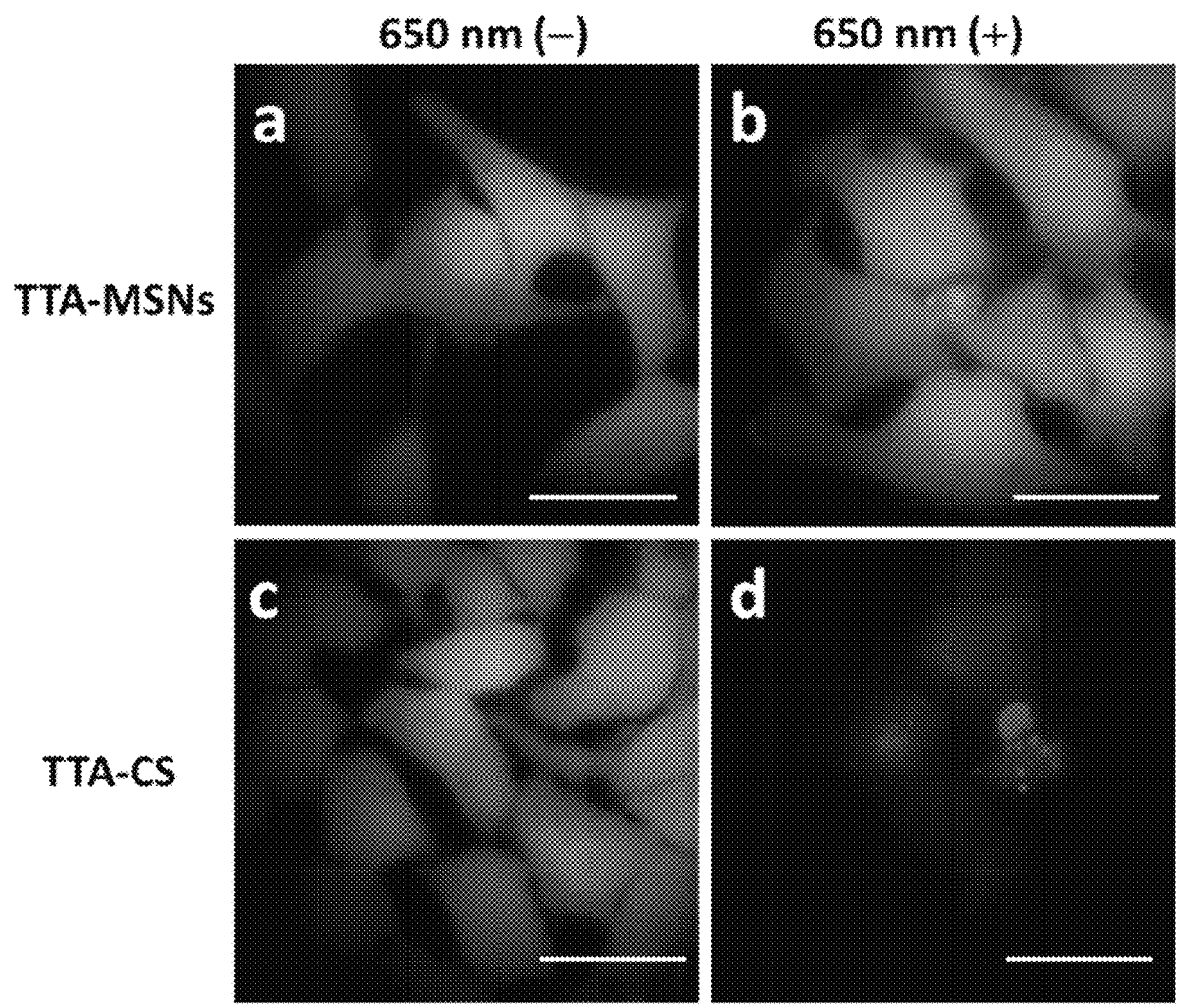
FIG. 21. Fluorescence microscopy observed the living and dead cells by calcein-AM/PI co-staining. (a) TTA-MSNs in the absence of light; (b) TTA-MSNs in the presence of light; (c) TTA-CS in the absence of light; (d) TTA-CS in the presence of light. $\lambda_{ex}$=650 nm LED, photon fluence (360 J/cm$^2$).

Far red light mediated prodrug photorelease was also evaluated by the calcein-AM/PI co-staining method. (Ji, et al. 2011 Angew. Chem. Int. Ed. 50, 1626-1629.) In the absence of far-red LED irradiation, we only observed bright green emission in the cancer cells, suggesting that TTA-CS itself did not kill cancer cells. However, In the presence of far-red LED irradiation, red emission suggesting the cell deaths was observed in the cells. As a control, we did not observe significant cell death with prodrug-free core nanoparticles (TTA-MSNs) in the presence of LED irradiation (FIG. 21). These results further demonstrated that far-red light triggered TTA upconversion can activate prodrug photorelease and lead to cancer cells growth inhibition.

Since TTA-CS showed excellent cancer cell inhibition in vitro, we then continue testing TTA-UC-induced prodrug release in vivo. First, we prepared 4T$_1$ tumor-bearing mice and divided them into four experiment groups (Group 1: only PBS injection+irradiation; Group 2: TTA-CS injection but no irradiation; Group 3: TTA-MSNs and irradiation; Group 4: TTA-CS injection and irradiation). After 60 min. of intra-tumor injection, tumor sites were then irradiated with a far-red LED (100 mW/cm$^2$). The treatment outcome of TTA-CS to tumor was assessed by monitoring relative tumor volumes in mice, and tumor tissue ablation was also evaluated by H&E staining on tissue sections.

Figure 4:
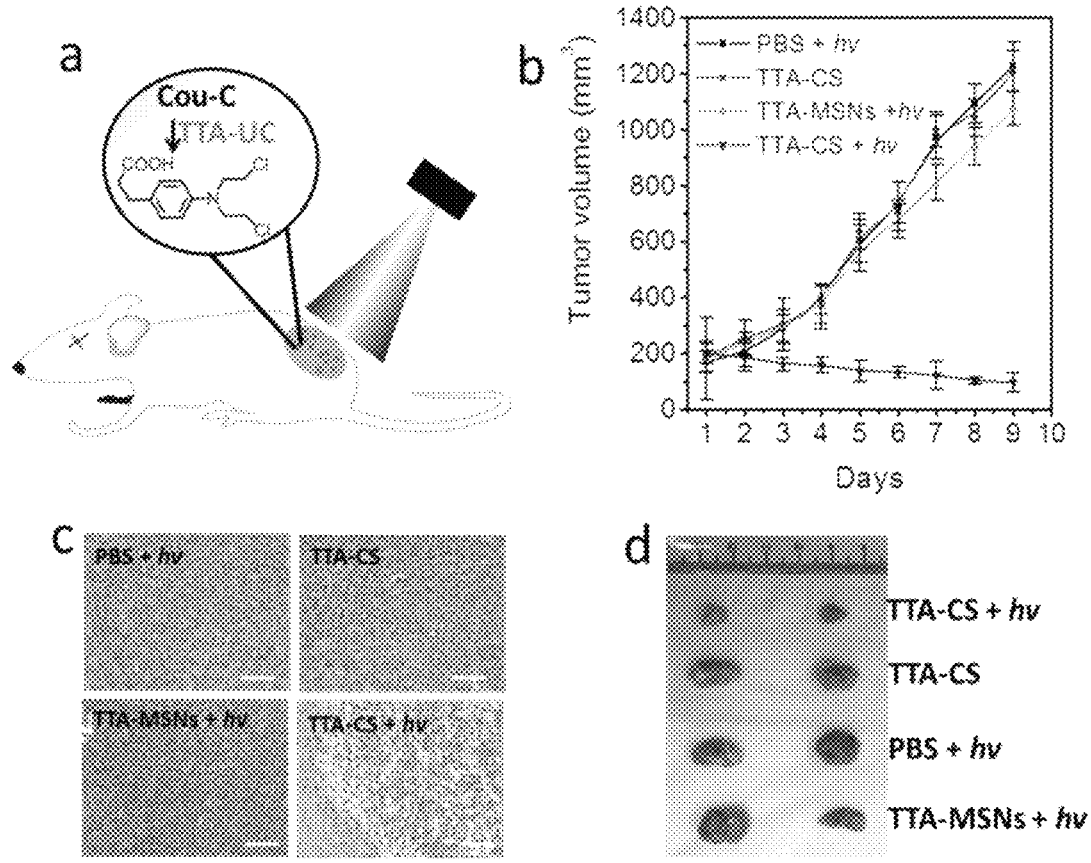
FIG. 4. (a) Illustration of the photocleavage drug release via TTA-UC; (b) Tumor growth inhibition by TTA-CS-mediated drug release in $4T_1$ tumors; Values are means±s.e.m. (n=5 mice per group) (c) H&E staining of tumor tissue sections from different treatment groups after 9 days of treatment, scar bar is 50 μm. (d) Representative digital photos of tumors for the four groups of mice. Photon fluence (180 J/cm²).

As shown in FIG. 4, no tumor growth inhibition or tumor tissue necrosis was observed in Group 1. Group 2 showed no tumor growth inhibition or tumor tissue necrosis, which indicates that TTA-CS itself cannot inhibit tumor growth. Group 3 also demonstrated insignificant cancer treatment efficiency, suggesting low power red LED we used has little photothermal or other effects for cancer cell killing. In marked contrast, the tumor growth in Group 4 was remarkably suppressed, and the tumor tissue showed obvious necrosis. These results indicate that the deep blue upconversion induced chlorambucil release from the prodrug (Cou-C) does lead to tumor tissue ablation. To the best of our knowledge, this is the first time that TTA-UC-induced photocleavage-based prodrug photorelease has been realized in vivo upon low power far-red LED irradiation.

Figure 22:
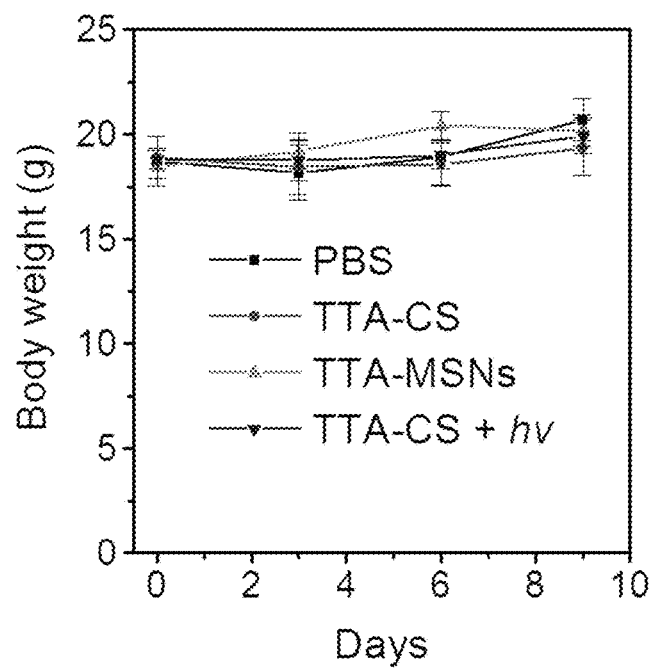
FIG. 22. The change of body weight of mice in the different conditions.
Figure 23:
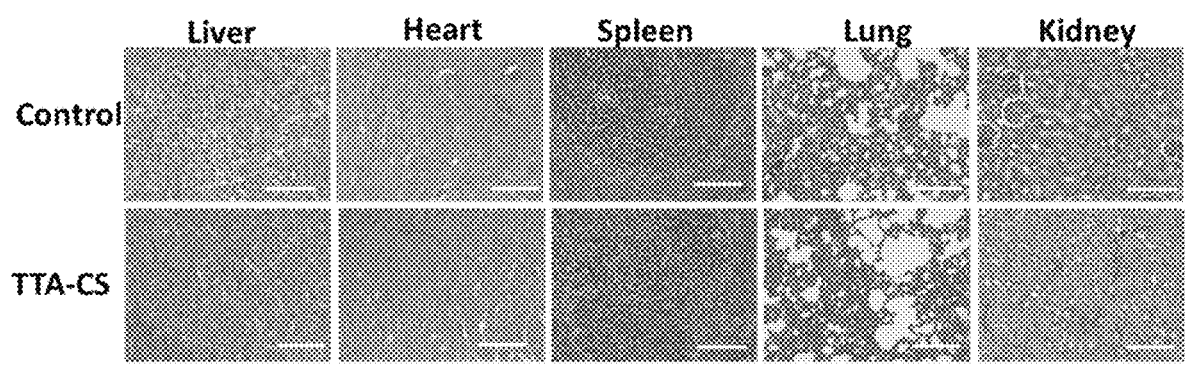
FIG. 23. H&E stained images of tissue sections from different organs of mice with introtumor injection of TTA-CS, 9 days after drug release to eliminate tumors. Scale bars: 100 μm.
Figure 24:
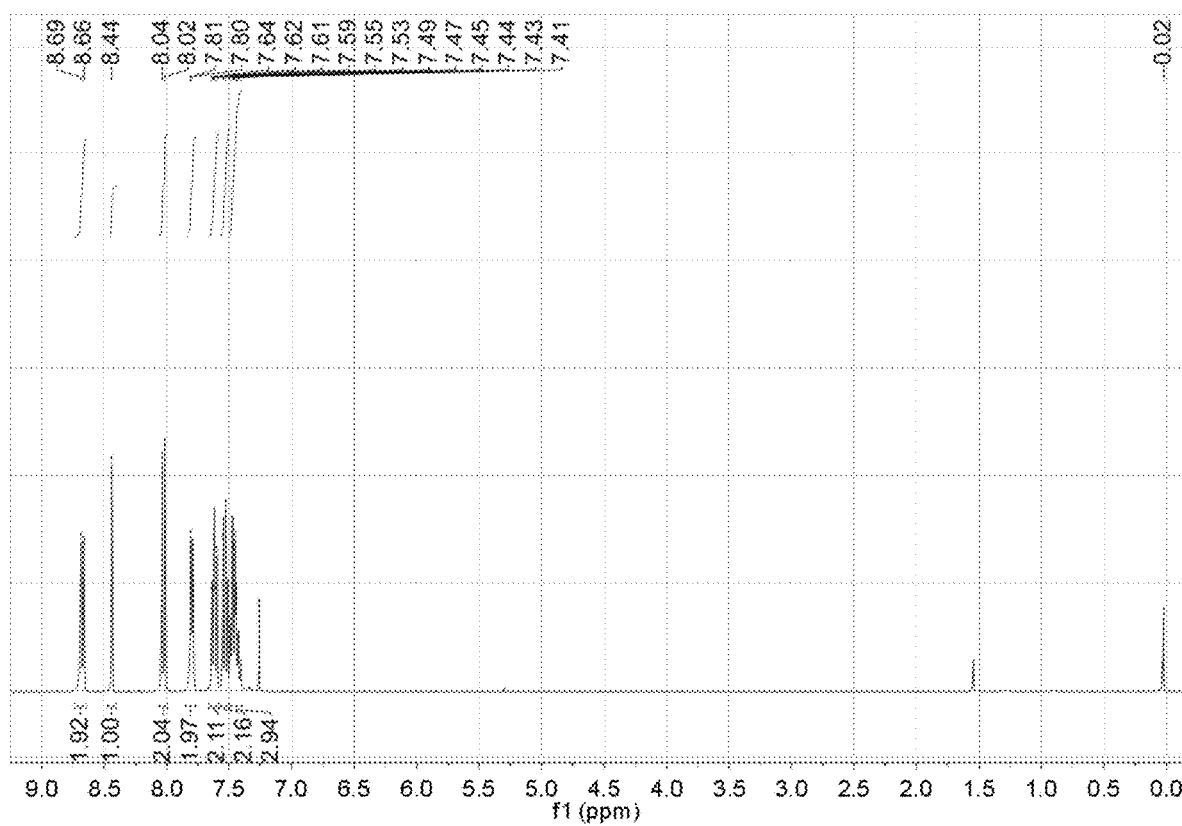
FIG. 24. $^1$HNMR of PEA (400 MHz, CDCl$_3$).
Figure 25:
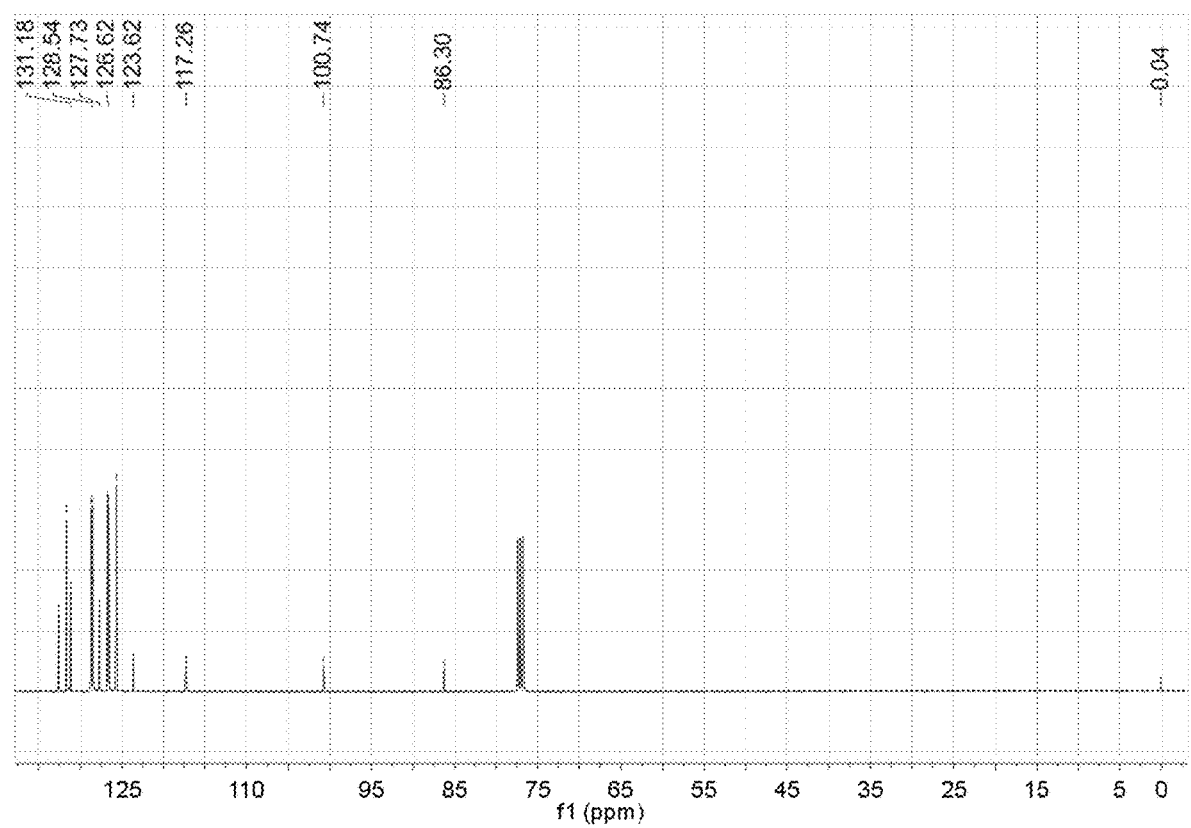
FIG. 25. $^{13}$CNMR of PEA (100 MHz, CDCl$_3$).
Figure 26:
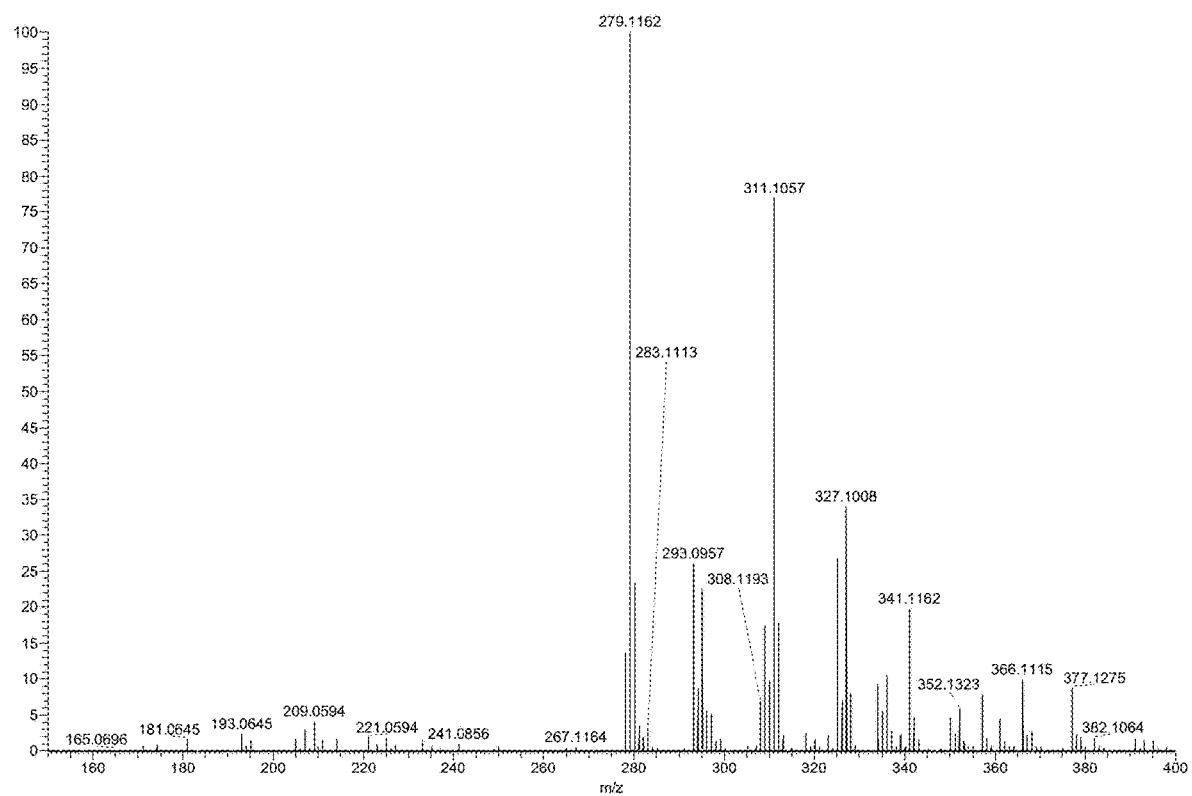
FIG. 26. ESI-HRMS of PEA.
Figure 27:
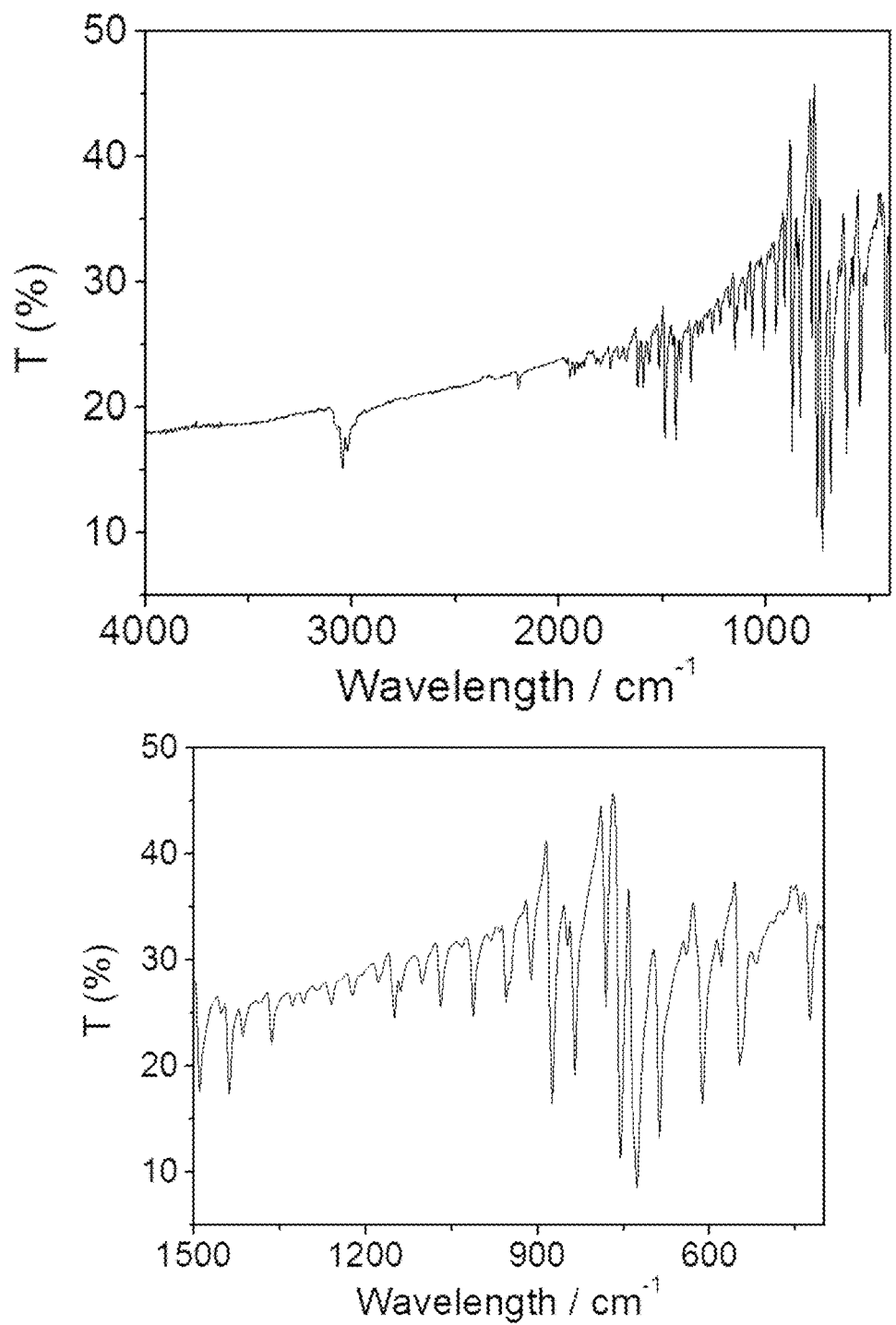
FIG. 27. FT-IR of PEA (KBr).
Figure 28:
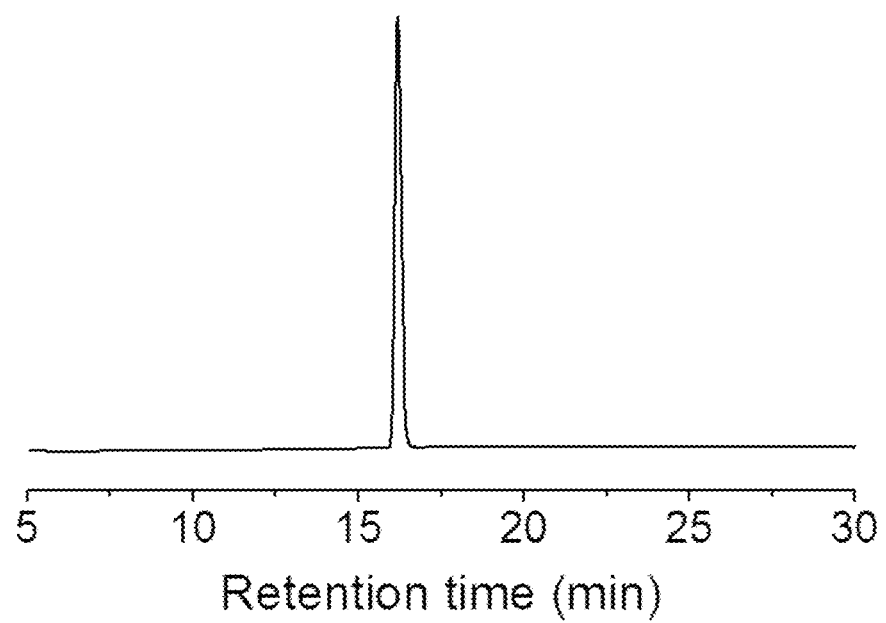
FIG. 28. HPLC of PEA (C$_{18}$ reverse column, eluent CH$_3$CN containing 0.1% TFA).
Figure 29:
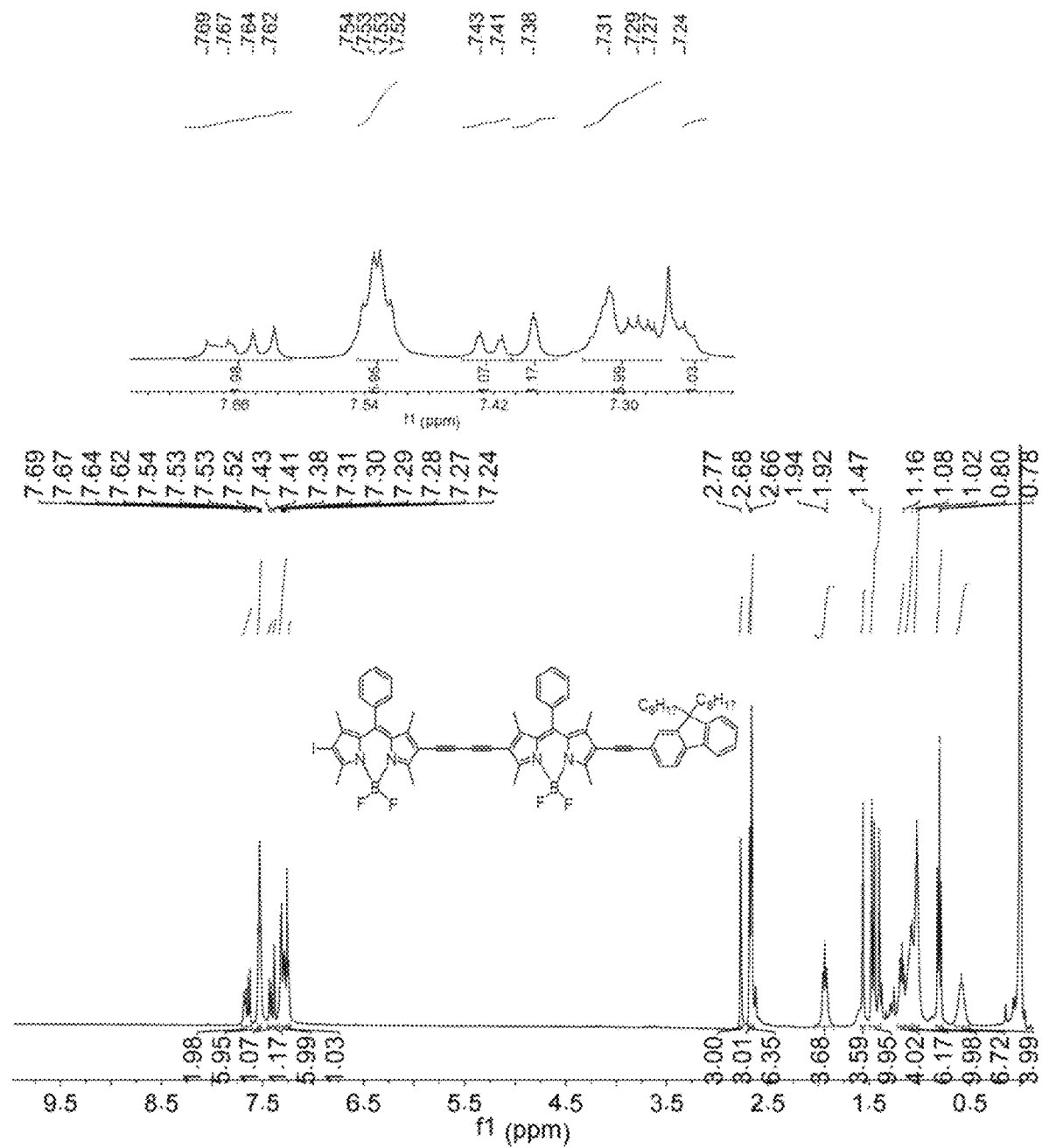
FIG. 29. $^1$HNMR of BDP-F (400 MHz, CDCl$_3$).
Figure 30:
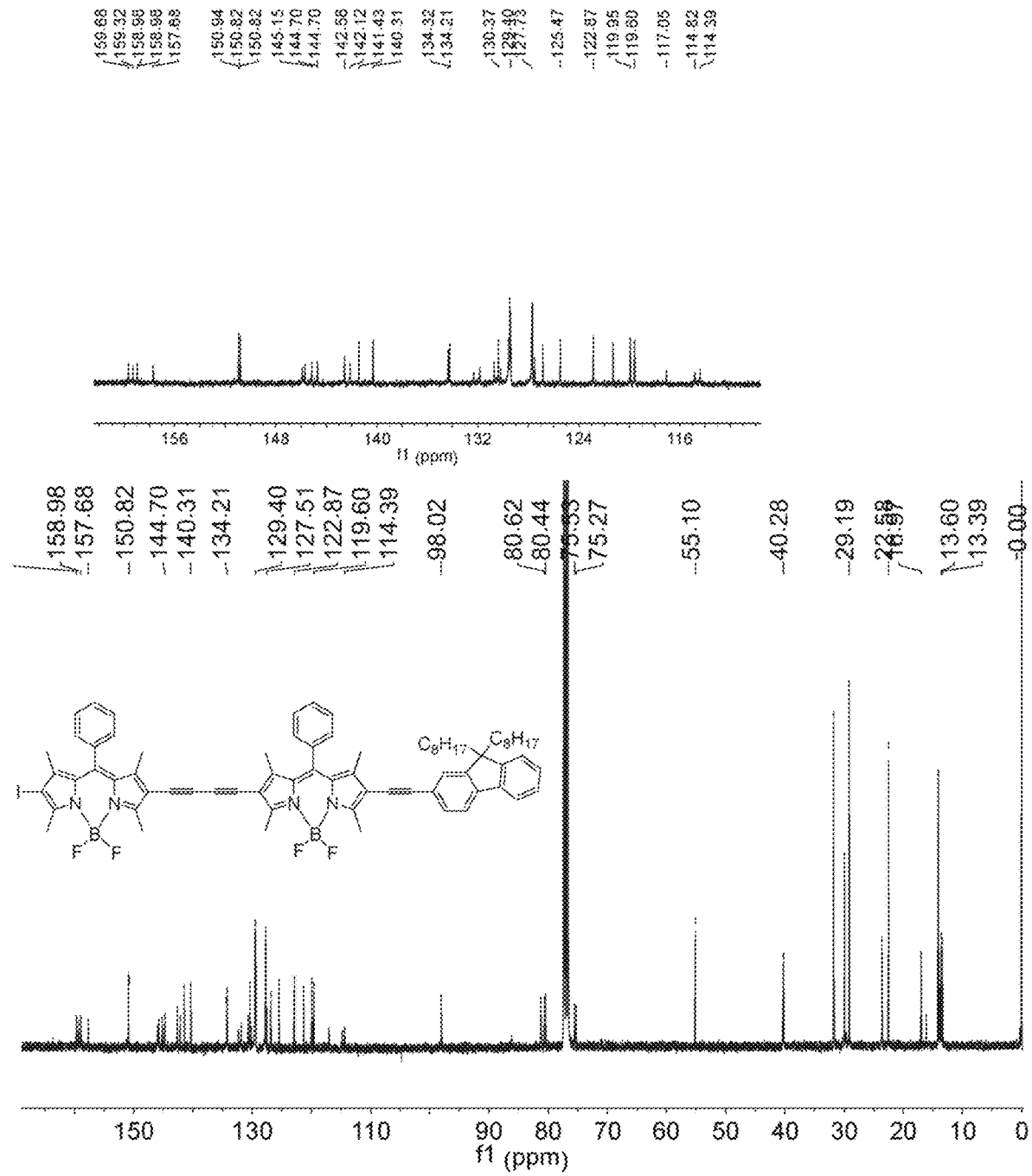
FIG. 30. $^{13}$CNMR of BDP-F (100 MHz, CDCl$_3$).
Figure 31:
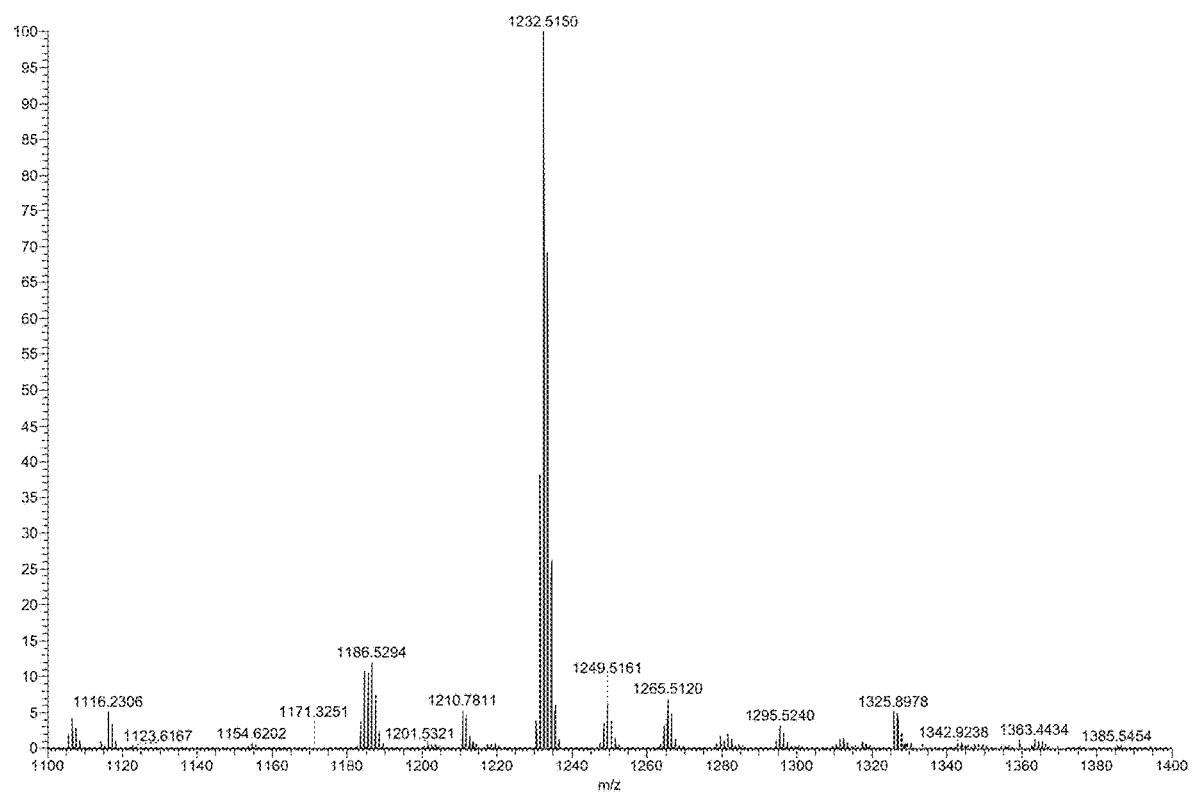
FIG. 31. ESI-HRMS of BDP-F.
Figure 32:
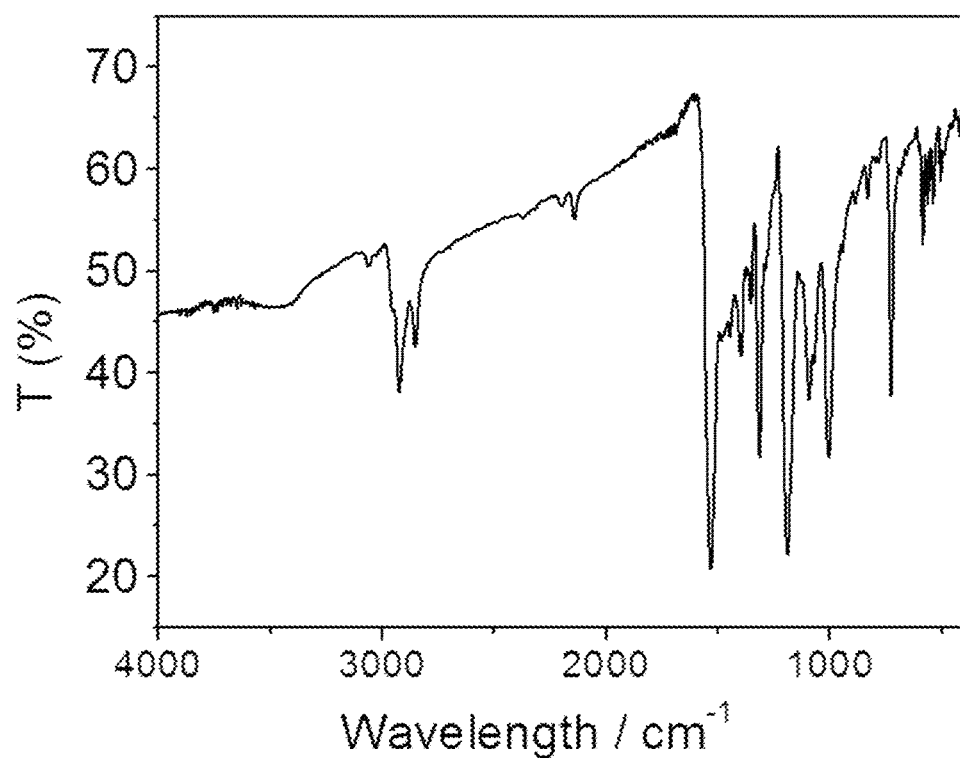
FIG. 32. FT-IR of BDP-F (KBr).
Figure 33:
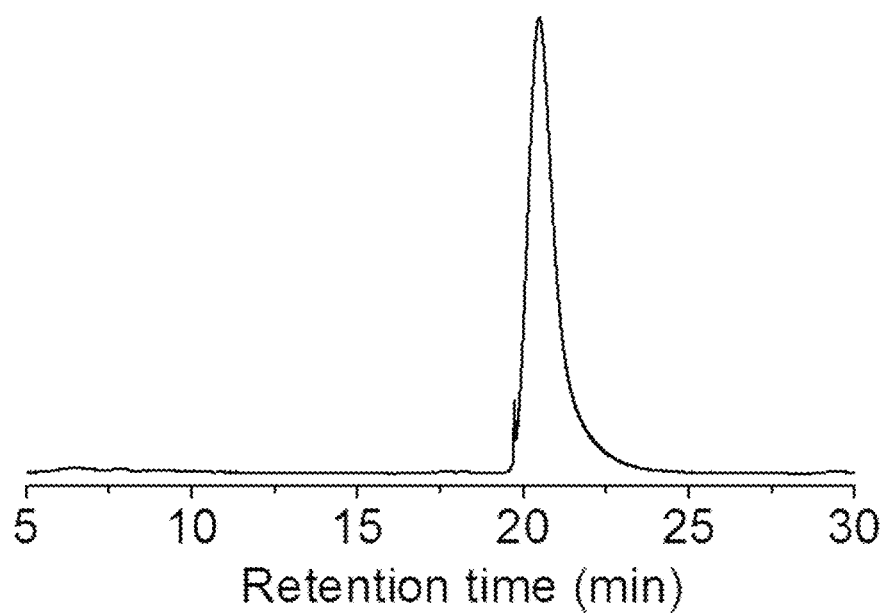
FIG. 33. HPLC of PEA (C$_{18}$ reverse column, eluent CH$_3$CN containing 0.1% TFA).

In order to determine the potential toxicity and side effects of TTA-CS, the mice's body weight loss was measured. As shown in FIG. 22, mice treated with TTA-CS did not show apparent weight loss. After 9 days by an intravenous injection of TTA-CS, the treated mice and untreated age-matched healthy mice were sacrificed, and the major organs including heart, liver, spleen, lung, and kidney were collected for H&E staining to evaluate the toxic effect. No noticeable sign of organ damage was observed on the H&E-stained organ slices, which suggests that TTA-CS is safe for in vivo cancer treatment applications (FIG. 23). Further, the serum analysis experiment was performed, as shown in Table 2, and no abnormal results were observed from this serum analysis, which suggests that no observable inflammation was induced.

TABLE 2

Blood biochemistry and complete blood panel analysis of mice

| | Normal range | Control group | Experiment group |
|---|---|---|---|
| WBC (K/μL) | 1.8-10.7 | 6.34 | 10.12 |
| NE (K/μL) | 0.1-2.4 | 1.90 | 1.55 |
| LY (K/μL) | 0.9-9.3 | 3.68 | 6.91 |
| MO (K/TL) | 0.0-0.4 | 0.22 | 0.38 |
| EO (K/μL) | 0.0-0.2 | 0.19 | 0.14 |
| BA (K/μL) | 0.0-0.2 | 0.15 | 0.04 |
| RBC (M/μL) | 6.36-9.42 | 7.70 | 7.69 |
| HGB (g/dL) | 11.0-15.1 | 12.7 | 12.3 |
| HCT (%) | 35.1-45.4 | 42.9 | 42.4 |
| MCV (fL) | 45.4-60.3 | 55.7 | 55.1 |
| MCH (pg) | 14.1-19.3 | 16.5 | 16.0 |
| MCHC (K/μL) | 30.2-34.2 | 30.6 | 31.0 |
| RDW (K/μL) | 12.4-27.0 | 15.3 | 15.9 |
| PLT (K/μL) | 592-2972 | 654 | 670 |
| MPV (fL) | 5.0-20.0 | 5.5 | 5.2 |

White blood cell (WBC),
Neutrophils (NE),
Lymphocytes (LY),
Monocytes (MO),
Eosinophils (EO),
Basophils (BA),
Red blood cell (RBC),
Hemoglobin (HGB),
Hematocrit (HCT),
Mean corpuscular volume (MCV),
Mean corpuscular hemoglobin (MCH),
Mean corpuscular hemoglobin concentration (MCHC),
Red blood cell distribution width (RDW),
Platelet Thrombocyte (PLT),
Mean platelet volume (MPV).

EXPERIMENTAL

Chemicals and Instruments

All reagents and solvents were used as received without further purification unless otherwise indicated. Methyl oleate, 2,4-dimethylpyrrole, trimethylsilylacetylene, copper iodide, dichlorobistriphenylphosphine palladium (Pd(PPh$_3$)Cl$_2$), 9-bromo-anthracene, phenylacetylene, dry tetrahydrofuran (THF) were purchased from Sigma-Aldrich. Analytical grade toluene, methanol, CHCl$_3$, CH$_2$Cl$_2$, THF, and dimethylformamide (DMF) were purchased from Fisher Scientific. Deionized water was used in the experiments.

The compounds were characterized by $^1$H-NMR, $^{13}$C-NMR, ESI-HRMS and FT-IR. The purified of BDP-F and PEA was characterized by HLPC (C$_{18}$ reverse phase column, eluent: CH$_3$CN containing 0.1% TFA). $^1$H-NMR and $^{13}$C-NMR spectra were obtained on a Bruker 400 MHz NMR spectrometer, tetramethylsilane (TMS) as internal standard (0 ppm) substances, and CDCl$_3$ as solvent. Agilent Cary 5, UV-Vis spectrometer was used to measure the UV-vis absorption spectra, and a HITACHI F-7000 fluorescence spectrometer with 450 W xenon lamps was utilized to obtain the steady-state emission spectra and Fluorescence lifetimes were measured on an OB920 luminescence lifetime spectrometer.

The nanosecond time resolved transient absorption spectra were detected by an LP920 laser flash photolysis spectrometer. The transient signals were recorded on a digital oscilloscope. The lifetime values by monitoring the decay trace of the transients were obtained with LP900 software.

All samples in flash photolysis experiments were deaerated with Ar for ca. 15 min. before measurement, and the gas flow was maintained during the measurements. The morphology of the TTA-MSNs nanoparticles was characterized at a JEOL JEM-200CX transmission electron microscope (TEM) operated at 80 kV.

The sample for TEM measurement was prepared by dropping the solution onto a carbon coated copper grid. The particle size and size distribution of TTA-CS and TTA-MSNs were measured by dynamic light scattering (DLS) using a Mastersizer 2000 particle size analyzer, laser wavelength is 633 nm. For the TTA upconversion spectra measurement, the diode pumped solid-state laser (650 nm, continues wave, CW, Hi-Teach company, China) was used to excitation light source, and a modified spectrofluorometer was used to record the upconversion spectra. For the prodrug photorelease experiment, a far red LED (Mightex Company, 650 nm, 100 mW/cm$^2$) as excitation light source was used.

Scheme 4. Synthesis of BDP-F and molecular structure of PEA.$^a$

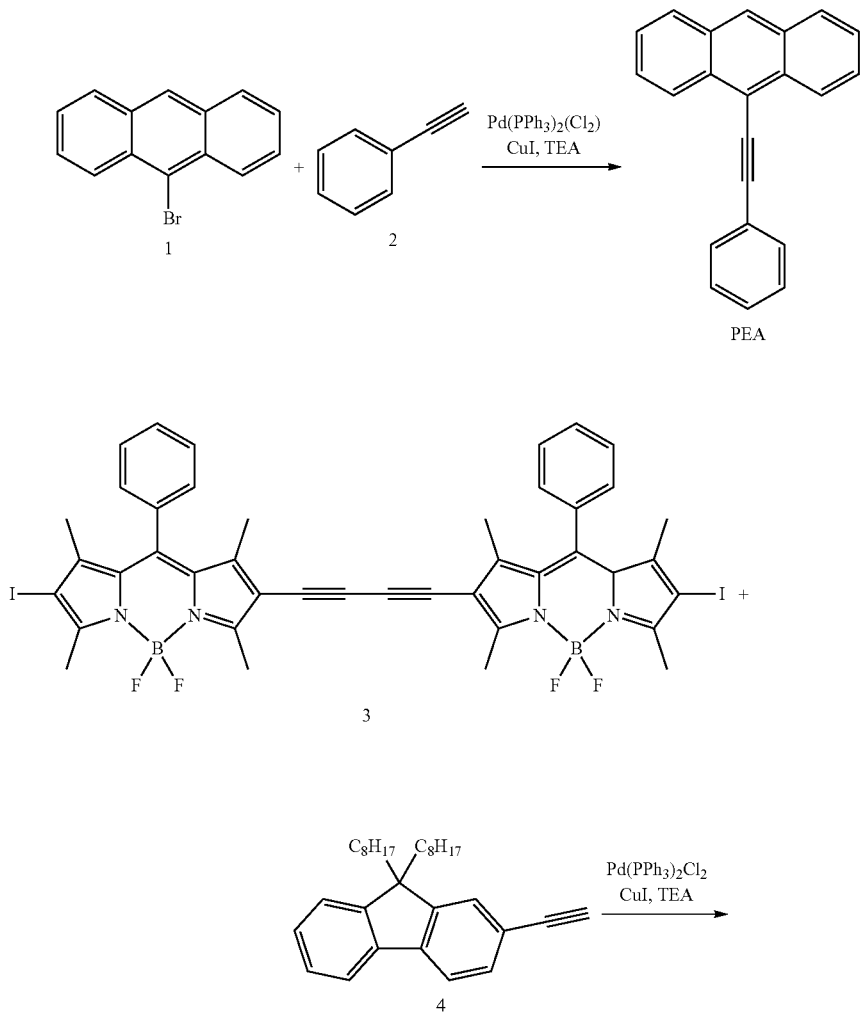

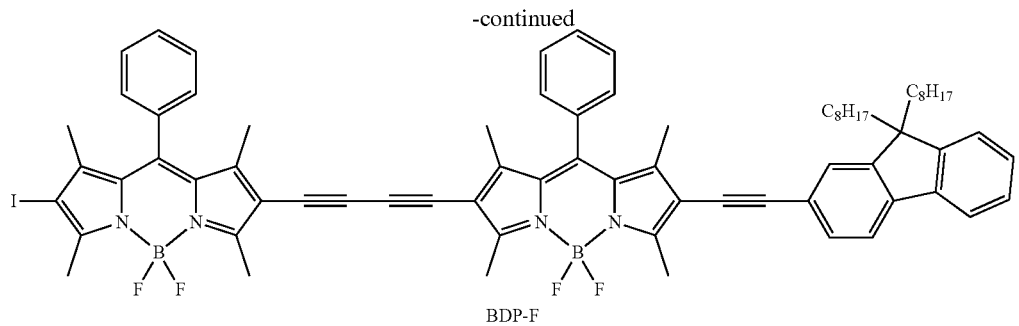

BDP-F

Compounds 3, 4, Cou-C were synthesized according to the previous synthesis protocols[1-4].

BDP-F:

Under Ar atmosphere, compound 3 (475 mg, 0.05 mmol) 2-ethynyl-11-Octyl-fluorene-4 (20.7, 0.05 mmol), Pd(PPh$_3$)$_2$Cl$_2$ (3.1 mg, 0.005 mmol), PPh$_3$ (2.6 mg, 0.01 mmol), and CuI (2.0 mg, 0.01 mmol) were dissolved in a mixed solvent of THF/N-ethyldiisopropylamine (10 mL/3 mL), and the flask was degassed many times by freezer-pump way. The mixture was heated at 60° C. for 6 h. The solvent was removed under reduced pressure, and the crude product was purified by column chromatography (silica gel, hexane/CH$_2$Cl$_2$, 1:1, v/v). The dark blue band was collected, and evaporation of solvent gave a black solid (32.1 mg, 51%). $^1$H-NMR (400 Hz, CDCl$_3$): δ=7.69-7.66 (m, 1H), 7.64 (d, J=8.0 Hz, 1H), 7.54-7.52 (m, 6H), 7.43 (d, J=7.6 Hz, 1H), 7.38 (s, 1H), 7.33-7.27 (m, 6H), 7.24-7.23 (m, 1H), 2.77 (s, 3H), 2.68 (s, 3H), 2.66 (s, 6H), 1.96-1.92 (m, 4H), 1.54 (s, 3H), 1.47 (s, 3H), 1.45 (s, 3H), 1.40 (s, 3H), 1.19-1.16 (m, 4H), 1.09-1.02 (m, 16H), 0.82-0.78 (m, 6H), 0.58 ppm (s, 4H). $^{13}$C-NMR (100 Hz, CDCl3): δ=159.7, 159.3, 159.0, 157.7, 151.0, 150.8, 145.9, 145.7, 145.2, 144.7, 142.6, 142.1, 141.4, 140.3, 134.3, 134.2, 132.3, 131.9, 130.7, 130.4, 130.2, 129.6, 129.5, 129.4, 129.3, 127.7, 127.6, 127.5, 126.9, 125.5, 122.9, 121.3, 120.0, 119.6, 117.1, 114.8, 114.4, 98.0, 81.2, 80.6, 80.4, 75.5, 75.3, 55.1, 40.3, 31.8, 30.0, 29.2, 23.7, 22.6, 16.9, 16.1, 14.1, 13.9, 13.8, 13.6, 13.5, 13.4 ppm. ESI-HRMS (C$_{73}$H$_{76}$B$_2$F$_4$IN$_4$+ H+): calcd m/z=1233.5237; found m/z=1233.5250. FT-IR (KBr, cm$^{-1}$): ν=3063, 2922, 2848, 2198, 2136, 1528, 1393, 1313, 1196, 1092, 1012, 729, 582. Molar extinction coefficients (615 nm, ε=1.77×10$^5$M$^{-1}$ cm$^{-1}$), HPLC (C$_{18}$ reverse column, eluent: CH$_3$CN containing 0.1% TFA) retention time 22 min.

PEA:

9-bromoanthracene (1.0 mmol, 256 mg), phenylacetylene (2.0 mmol, 205 mg) were dissolved in TEA and THF (10 mL, 1/1, v/v). The solution was degassed 3 times and Pd(PPh$_3$)Cl$_2$ (0.05 mmol, 36 mg), PPh$_3$ (0.1 mmol, 26.2 mg) and CuI (1.0 mmol, 19.1 mg) were added. The reaction was heated to 70° C. for 24 h. The solvent was removed under reduced pressure, and the crude product was purified by column chromatography (silica gel, hexane/CH$_2$Cl$_2$, 100:10, v/v). The yellow band was collected, and evaporation of solvent gave a black solid (42.5 mg, 17%). $^1$H-NMR (400 Hz, CDCl$_3$): δ=8.69 (2H, d, J=8.0 Hz), 8.44 (s, 1H), 8.04 (2H, d, J=7.6 Hz), 7.81-7.80 (m, 2H), 7.64-7.61 (m, 2H), 7.53-7.47 (m, 2H), 7.45-7.41 ppm (m, 3H). $^{13}$C-NMR (100 Hz, CDCl$_3$): δ=132.6, 131.7, 131.2, 128.7, 128.5, 128.4, 127.7, 126.8, 126.6, 125.7, 123.6, 117.3, 100.7, 86.3 ppm. ESI-HRMS (C$_{22}$H$_{24}$+H+): calcd m/z=279.1174; found m/z=279.1162. FT-IR (KBr, cm$^{-1}$): ν=3048, 3025, 2201, 1487, 1438, 873, 835, 780, 753, 726, 690, 611, 548, 425. Molar extinction coefficients (400/419 nm, =1.5×10$^4$/1.4× 10$^4$M$^{-1}$ cm$^{-1}$) HPLC (C$_{18}$ reverse column, eluent: CH$_3$CN containing 0.1% TFA) retention time 16 min.

TTA Upconversion

Diode pumped solid-state laser (650 nm, continues wave, CW) was used for the upconversion. The diameter of the laser spot is 5 mm. For the upconversion experiments, the mixed solution of the BDP-F (sensitizer) and PEA (emitter) was degassed for at least 15 min. with Ar. Then the solution was excited with a laser. The upconverted fluorescence of PEA was recorded with spectrofluorometer.

The upconversion quantum yields (ψ$_{UC}$) were determined with the prompt fluorescence of methyl blue as the standard (Φ$_F$=3% in methanol). The upconversion quantum yields were calculated with the Eq. 1, where Φ$_{UC}$ and Φ$_{std}$ stand for upconversion luminescence quantum yield of sample TTA-UC and fluorescence quantum yield of methyl blue, respectively. A$_{unk}$ and A$_{std}$ stand for absorbance of the TTA-UC and methyl blue, respectively. I$_{unk}$ and I$_{std}$ stand for integrated upconversion luminescence intensity of the TTA-UC and fluorescence intensity of methyl blue, respectively. I$_{unk}$ and η$_{std}$ stand for the refractive index of water, The equation is multiplied by a factor of 2 to make the maximum quantum yield to be unity.

$$\Phi_{UC} = 2 \times \Phi_{std} \times \frac{A_{std}}{A_{unk}} \times \frac{I_{unk}}{I_{std}} \times \left(\frac{\eta_{unk}}{\eta_{std}}\right)^2 \quad \text{Eq. 1}$$

Triplet excited state lifetime of BDP-F measurement. The triplet excited state lifetime of BDP-F was measured on an LP 920 laser flash photolysis spectrometer (Edinburgh Instruments, U.K.) and recorded on a Tektronix TDS 3012B oscilloscope. The lifetime values (by monitoring the decay trace of the transients) were obtained with the LP900 software. The sample in flash photolysis experiments was deaerated with argon for ca. 15 min. before measurement, and the argon gas flow was kept during the measurement.

Preparation of TTA-MSNs Nanoparticles

Firstly, MSNs silica nanoparticles were synthesized according to following steps. CTAB (2.00 g, 5.58 mmol) was dissolved in 1000 mL of DI water. Sodium hydroxide aqueous solution (2.00M, 7.0 mL) was introduced to the CTAB solution, and the temperature of the mixture was adjusted to 80° C. TEOS (10.00 mL, 45.0 mmol) was added dropwise to the surfactant solution under vigorous stirring. The mixture was allowed to react for 2 h to give a white precipitate. This solid crude product was filtered, washed with deionized water and methanol, and dried in air to yield the as-synthesized mesoporous silica nanoparticles (denoted as MSN). To remove the surfactant template (CTAB), 1.50 g of the as-synthesized MSN was refluxed for 24 h in a methanolic solution of 9.00 mL of HCl (37.4%) in 160.00 mL of methanol. The resulting material was filtered and extensively washed with deionized water and methanol. The filter was dried under vacuum for 24 h at room temperature.

Next, TTA-MSNs were prepared dependence on the following steps. MSNs (50.0 mg) were dispersed 25 mL round flask in of BDP-F (2 mg), PEA (3 mg) and methyl oleate (150 mg) in THF (10 mL). The mixture solution was stirred until organic solvent evaporation (about 12 h) at room temperature in the dark condition. And then 10 mL PBS buffer was added. The mixture was ultrasonic shocked for 20 min. to make the nanoparticles dispersed in the PBS buffer. Then the BDP-F (sensitizer) and PEA (emitter)-loaded silica nanoparticles were low speed centrifuged (1000 rpm/min) for 5 min. The supernatant was collected and then extracted using dichloromethane (DCM). The DCM solvent containing BDP-F and PEA was used to measure sensitizer and emitter loading by collecting UV-vis absorption spectra using a molar absorption coefficient of 177500 $M^{-1}$ $cm^{-1}$ with $\lambda_{max}$=615 nm for BDP-F, 18000 $M^{-1}$ $cm^{-1}$ with $\lambda_{max}$=420 nm for PEA. Sensitizer and emitter loading were calculated using the following equation:

Entrapment efficiency (%)=absorption of the loaded dye/absorption initial mass of the dye×100%.

The entrapment efficiency of BDP-F is 61%, the entrapment efficiency of PEA is 72%.

The precipitate containing sensitizer and emitter nanoparticles (TTA-MESNs) were collected and then dried (40° C.) in the vacuum condition for 24 h in the dark condition. At last, the dried TTA-MSNs was dispersed in PBS buffer by using ultrasonic shock for 30 min., the concentration of TTA-MSNs is 5 mg/mL. The size of the TTA-MSNs was measured by DLS in an aqueous suspension at 1 mg/mL of MSN in DI water, laser wavelength is 633 nm.

Preparation of TTA-CS

Cou-C (3 mg), TTA-MSNs (30 mg) and pluronic F-127 (120 mg) were dissolved in THF/toluene (1/1, v/v, 8 mL). The organic solvents were dried in the vacuum for 2 h at 35° C. in the dark condition (note: all organic solvents should be removed). Then 15 mL PBS buffer was added. The mixture was stirred for 4 h (800 rpm/min) in the dark condition to make sure the solid dispersion. The mixture solution was low speed centrifuged (1000 rpm/min) for 5 min. to remove the big size nanocapsule. The supernatant (TTA-CS) were carefully collected. And then the supernatant was filtrated with 0.45 μm membrane to obtain sterile nanocapsule. Finally, the TTA-CS was stored at 4° C. refrigerator.

The precipitate sample was extracted with 10 mL DCM. And then absorbance of Cou-C was measured to calculate the entrapment efficiency.

Entrapment efficiency (%)=1−absorption of the unloaded prodrug/initial mass of the prodrug× 100%.

The entrapment efficiency of Cou-C is 79.0%

Far-red LED photocleave drug release of TTA-CS in solution. We found that the fluorescence of Cou-C reduced along with chlorambucil photoreleasing process at 498 nm. Based on the property, the photocontrollable chlorambucil releasing process also was monitored by measured the fluorescence spectra of Cou-C.

Cell Culture

Human cervical carcinoma (HeLa cell lines) and mice breast cancer cells (4T1 cell lines) were cultured in Dulbecco's modified Eagle's medium (DMEM) containing 10% fetal bovine serum (FBS), 100 μg $mL^{-1}$ streptomycin and 100 U $mL^{-1}$ penicillin at 37° C. in a humidified incubator containing 5% $CO_2$ and 95% air. The medium was replenished every other day and the cells were subculture after reaching confluence.

In Vitro Cytotoxicity Studies of TTA-CS Using Hela and 4T1 Cell Lines

We seeded Hela or 4T1 cells at a density of 5000 on the 96 well plates. After 5 h, The cells were then incubated with 0, 75, 150, 225, 300, 375 μg/mL of TTA-CS and control group (TTA-MSNs) in cell culture medium for 12 h at 37° C. and 5% $CO_2$. Then the cells were irradiated by far red 650 nm LED for 60 min. (100 mW/$cm^2$), photon fluene is 360 J/$cm^2$. After irradiation the cells were again incubated for 24 h. Then, 20 μL of 5 mg $mL^{-1}$ MTT solution in pH 7.4 PBS was added to each well. After 4 h incubation, the medium containing unreacted MTT was removed carefully, and 200 μL DMSO was added to each well to dissolve the produced blue formazan. After 30 min., the optical density (OD) at a wavelength of 595 nm was measured with Bio-Rad microplate reader. The percentage of growth inhibition was calculated with Eq. 2.

Cell viability (%)=OD value test/OD value control× 100% (Eq. 2)

Dead Cells and Living Cells Detection by Propidium Iodide (PI) and Calcein A.M Staining The cells (1×$10^5$) per well were seeded on confocal dish (35 mm) and incubated in complete medium for 24 h at 37° C. The medium was then replaced with fresh culture medium containing TTA-CS (400 μg/mL) to incubate for 12 h at 37° C. The cells were irradiated with a 650 nm far red light LED at a power of 100 mW/$cm^2$ for 60 min. (photon fluene 360 J/$cm^2$) and then culture another 24 h. Afterward, the cells were stained with PI and calcein A.M according to the manufacturer's instruction. After 20 min., the solution was removed and PBS used to wash cells at least three times. The dead cells were visualized with a wide field fluorescence microscopy (63× oil objective). Excitation wavelength was 549 nm. Emission detection wavelength region was 580-620 nm. The living cells was also observed, the excitation wavelength was 488 nm, the emission was 500-550 nm.

In Vivo Studies of TTA-CS for Tumor Inhibition in 4T1 Tumor-Bearing Mice

The mice were subjected to four different treatments: Group 1, PBS (200 μL) and far red LED irradiation; Group 2, intratumoral injection TTA-CS only (200 μL, 5 mg/mL); Group 3, intratumoral injection TTA-MSNs (200 μL, 1 mg/mL) and far red LED irradiation; Group 4, intratumoral injection TTA-CS (200 μL, 5 mg/mL) combined with exposure far red LED. After 1 h, far red light LED (650 nm) was performed on groups 1, 3, 4 at 100 mW $cm^{-2}$ for 30 min. (photon fluene 180 J/$cm^2$). Two mice from each group were euthanized 9 d post-treatment, and tumor tissues of the above-mentioned treatment Groups 1-4 were harvested for histological study by H&E staining under a BX51 optical microscope (Olympus, Japan) in a blinded fashion by a pathologist. Different treatment groups were monitored by measuring the tumor size using a Vernier caliper for 9 d. Tumor size=width×width×length/2.

Scheme 5

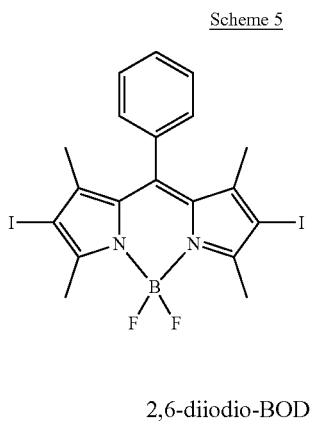

2,6-diiodio-BODIPY

Molecular Structure of 2,6-diiodio-BODIPY

FIG. 34 depicts an illustration of the preparation of TTA-CS, and TTA-UC mediated prodrug activation.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. An upconversion composition, comprising an organic triplet photosensitizer molecule and an organic emitter molecule, wherein the composition is characterized by an upconversion upon excitation in the red region of about 500 nm to about 600 nm or far red region of about 600 nm to about 700 nm with an emission in the deep blue region of about 410 nm to about 550 nm, wherein each of the triplet photosensitizer and emitter molecules comprises no metallic elements, wherein the triplet photosensitizer molecule has the structural formula (I):

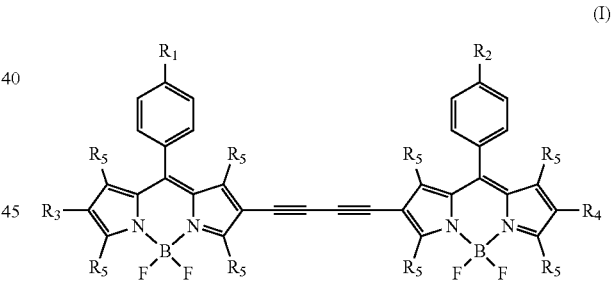

(I)

wherein
each of $R_1$ and $R_2$ is independently selected from the group consisting of: H, bromo, iodio, alkynyl, alkyl, alkenyl, azide, PEG, amino, carboxyl acid and hydroxyl;
$R_3$ is selected from the group consisting of: bromo and iodio;
$R_4$ is an arylethynyl group; and
each $R_5$ is independently selected from the group consisting of: H and alkyl.

2. The composition of claim 1, wherein the emitter molecule is 9-phenylacetylene anthracene or a derivative thereof.

3. The composition of claim 2, wherein $R_4$ is selected from the group consisting of: phenylethynyl, naphthalene ethynyl, carbazole ethynyl and fluorenyl ethynyl.

4. The composition of claim 3, wherein $R_4$ is selected from the group consisting of:

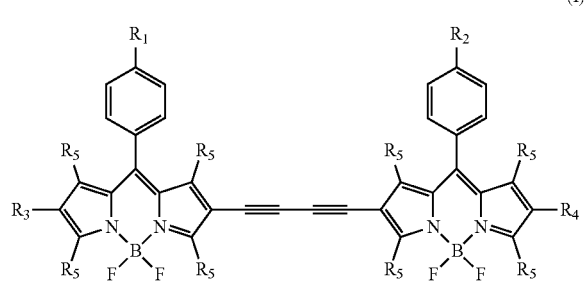

wherein each $R_6$ is independently a $C_2$-$C_{16}$ alkyl group.

5. A compound having the structural formula (I):

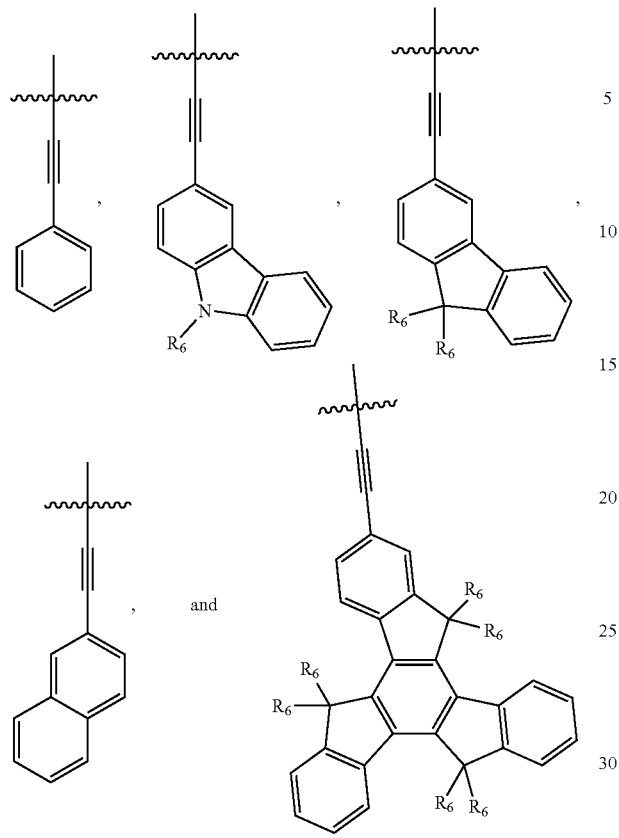

wherein
- each of $R_1$ and $R_2$ is independently selected from the group consisting of: H, bromo, iodio, alkynyl, alkyl, alkenyl, azide, PEG, amino, carboxyl acid and hydroxyl;
- $R_3$ is selected from the group consisting of: bromo and iodio;
- $R_4$ is an arylethynyl group; and
- each $R_5$ is independently selected from the group consisting of: H and alkyl.

6. A biocompatible nanoparticle delivery system, comprising:
- a triplet photosensitizer molecule and an emitter molecule, wherein
  each of the triplet photosensitizer and emitter molecules is an organic molecule and comprises no metallic elements;
- the triplet photosensitizer is excited by a light in the red region of about 500 nm to about 600 nm or far red region of about 600 nm to about 700 nm causing an emission by the emitter molecule in the deep blue region of about 410 nm to about 550 nm; and
- a photolabile molecule comprising a biologically active agent, wherein the biologically active agent is releasable upon absorption of the emission by the emitter molecule, wherein the triplet photosensitizer molecule has the structural formula (I):

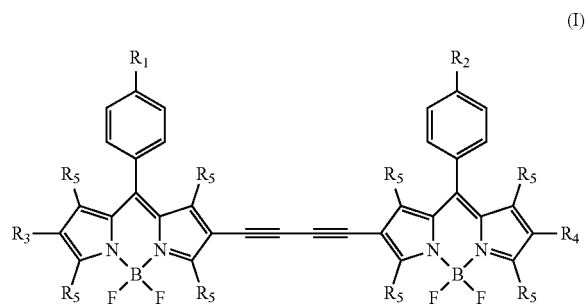

wherein
- each of $R_1$ and $R_2$ is independently selected from the group consisting of: H, bromo, iodio, alkynyl, alkyl, alkenyl, azide, PEG, amino, carboxyl acid and hydroxyl;
- $R_3$ is selected from the group consisting of: bromo and iodio;
- $R_4$ is an arylethynyl group; and
- each $R_5$ is independently selected from the group consisting of: H and alkyl.

7. The nanoparticle delivery system of claim 6, wherein the nanoparticle is characterized by a core-shell structure, wherein the triplet photosensitizer molecule and an emitter molecule are deposed in the core whereas the photolabile molecule is deposed in the shell.

8. The nanoparticle delivery system of claim 6, wherein the emitter molecule is 9-phenylacetylene anthracene.

9. The nanoparticle delivery system of claim 8, wherein $R_4$ is selected from the group consisting of: phenylethynyl, naphthalene ethynyl, carbazole ethynyl and fluorenyl ethynyl.

10. The nanoparticle delivery system of claim 9, wherein $R_4$ is selected from the group consisting of:

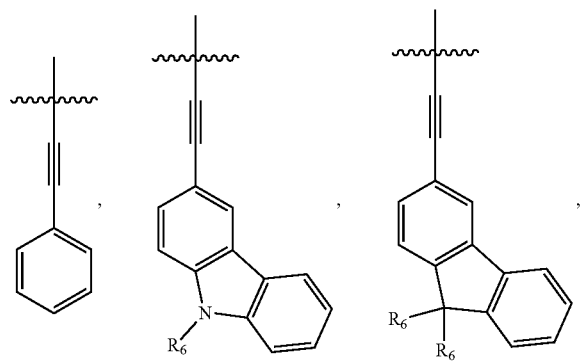

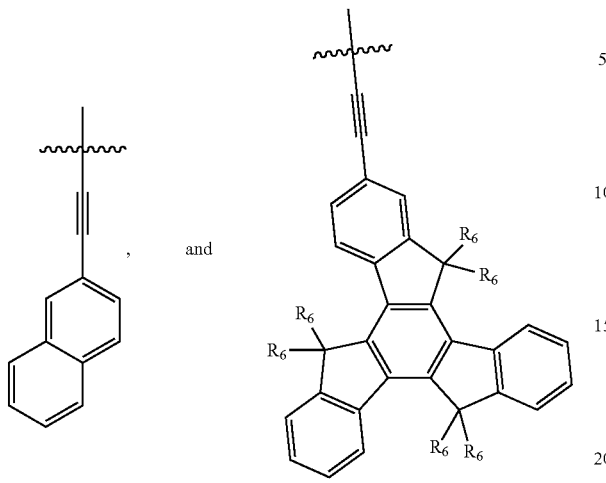

wherein each $R_6$ is independently a $C_2$-$C_{16}$ alkyl group.

11. The nanoparticle delivery system of claim 6, wherein the biologically active agent is an anti-cancer agent.

12. The nanoparticle delivery system of claim 6, wherein the photolabile molecule comprises a coumarin moiety.

13. The nanoparticle delivery system of claim 11, wherein the anti-cancer agent is chlorambucil.

14. A pharmaceutical composition comprising a nanoparticle delivery system of claim 6.

15. The compound of claim 5, wherein $R_4$ is selected from the group consisting of: phenylethynyl, naphthalene ethynyl, carbazole ethynyl and fluorenyl ethynyl.

16. The compound of claim 15, wherein $R_4$ is selected from the group consisting of:

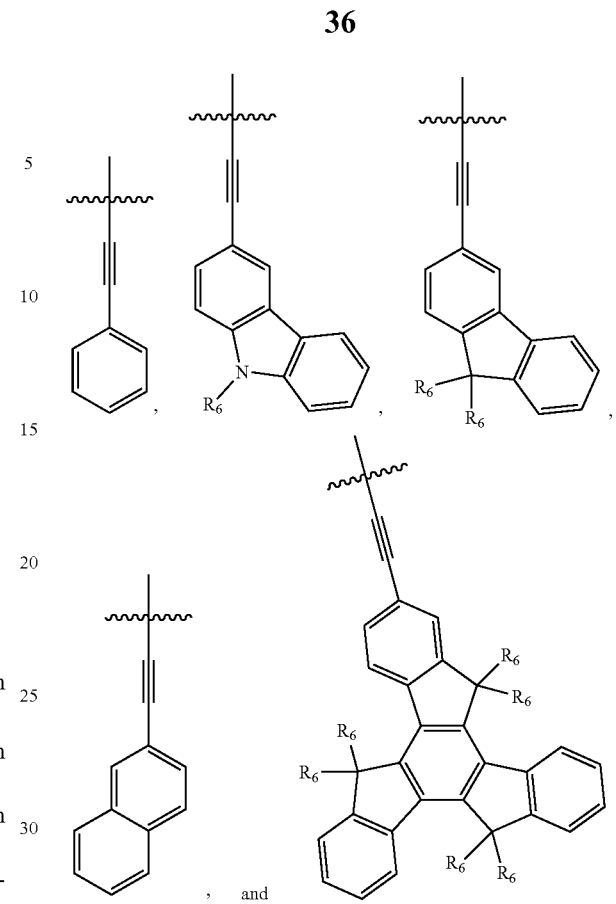

wherein each $R_6$ is independently a $C_2$-$C_{16}$ alkyl group.

17. The compound of claim 16, wherein each of $R_1$ and $R_2$ is H, $R_3$ is I, $R_4$ is a substituted or unsubstituted fluorenyl ethynyl, and each $R_5$ is methyl.

* * * * *